United States Patent
Tsukagoshi et al.

(10) Patent No.: US 11,083,428 B2
(45) Date of Patent: Aug. 10, 2021

(54) MEDICAL IMAGE DIAGNOSIS APPARATUS

(71) Applicant: CANON MEDICAL SYSTEMS CORPORATION, Otawara (JP)

(72) Inventors: Shinsuke Tsukagoshi, Nasushiobara (JP); Takahiro Goto, Utsunomiya (JP); Go Mukumoto, Obu (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 15/906,435

(22) Filed: Feb. 27, 2018

(65) Prior Publication Data

US 2018/0184997 A1 Jul. 5, 2018

Related U.S. Application Data

(63) Continuation of application No. PCT/JP2017/017605, filed on May 9, 2017.

(30) Foreign Application Priority Data

May 9, 2016 (JP) .............................. JP2016-094082

(51) Int. Cl.
*A61B 6/00* (2006.01)
*A61B 5/055* (2006.01)
(Continued)

(52) U.S. Cl.
CPC ............ *A61B 6/463* (2013.01); *A61B 5/0033* (2013.01); *A61B 5/055* (2013.01); *A61B 6/032* (2013.01);
(Continued)

(58) Field of Classification Search
CPC ............ G06T 7/74; G06T 2207/30004; G06T 7/0014; G06K 7/0012; A61B 6/4435;
(Continued)

(56) References Cited

U.S. PATENT DOCUMENTS 8,126,231 B2 2/2012 Sakaida
8,285,012 B2 * 10/2012 Kadomura ............ G06T 7/0012
345/419
(Continued)

FOREIGN PATENT DOCUMENTS

JP 2005-58526 3/2005
JP 2007-7255 1/2007
(Continued)

OTHER PUBLICATIONS

International Search Report dated Jul. 25, 2017 in PCT/JP2017/017605, filed on May 9, 2017.
(Continued)

*Primary Examiner* — Jingge Wu
(74) *Attorney, Agent, or Firm* — Oblon, McClelland, Maier & Neustadt, L.L.P.

(57) ABSTRACT

A medical image diagnosis apparatus according to an embodiment includes setting circuitry and image generating circuitry. The setting circuitry is configured to obtain position information with respect to a landmark of a patient in a first image generated by performing a first scan on the patient and to set a scan range to be used during a second scan by using the obtained position information, the position information being determined on a basis of the first image and expressed in an image taking system used during the first scan. The image generating circuitry is configured to generate a second image by performing the second scan on the scan range.

15 Claims, 19 Drawing Sheets

(51) Int. Cl.
 *A61B 5/00* (2006.01)
 *A61B 6/03* (2006.01)
 *G06T 7/00* (2017.01)

(52) U.S. Cl.
 CPC ............ *A61B 6/4435* (2013.01); *A61B 6/466* (2013.01); *A61B 6/469* (2013.01); *A61B 6/488* (2013.01); *A61B 6/5205* (2013.01); *A61B 6/5235* (2013.01); *A61B 6/5247* (2013.01); *A61B 6/545* (2013.01); *G06T 7/0012* (2013.01); *A61B 5/70* (2013.01); *A61B 6/405* (2013.01); *A61B 6/481* (2013.01); *G06T 2207/10081* (2013.01); *G06T 2207/10088* (2013.01); *G06T 2207/20101* (2013.01)

(58) Field of Classification Search
 CPC ....... A61B 6/466; A61B 6/5247; A61B 6/032; A61B 6/545; A61B 8/463; A61B 8/5292
 See application file for complete search history.

(56) References Cited

U.S. PATENT DOCUMENTS

| | | | |
|---|---|---|---|
| 8,386,273 B2 | 2/2013 | Kaminaga et al. | |
| 9,642,588 B2 | 5/2017 | Goto et al. | |
| 2007/0238963 A1* | 10/2007 | Kaminaga | A61B 6/032 600/407 |
| 2008/0025459 A1* | 1/2008 | Shi | A61B 6/032 378/10 |
| 2008/0025584 A1* | 1/2008 | Kunz | G06K 9/4638 382/128 |
| 2008/0242968 A1* | 10/2008 | Claus | A61B 6/032 600/407 |
| 2008/0317309 A1* | 12/2008 | Kazuno | G06F 19/321 382/128 |
| 2009/0147909 A1* | 6/2009 | Yoda | A61B 6/032 378/4 |
| 2009/0208105 A1* | 8/2009 | Bystrov | G01R 33/54 382/173 |
| 2012/0093383 A1* | 4/2012 | Claus | A61B 6/032 382/131 |
| 2013/0156151 A1* | 6/2013 | Sugaya | A61B 6/032 378/16 |
| 2014/0212016 A1* | 7/2014 | Kadomura | A61B 6/032 382/131 |
| 2014/0247284 A1* | 9/2014 | Gooding | G06T 7/174 345/642 |
| 2014/0253544 A1* | 9/2014 | Arakita | A61B 6/032 345/419 |
| 2014/0333617 A1* | 11/2014 | Miyamoto | A61B 34/10 345/420 |
| 2015/0051489 A1* | 2/2015 | Caluser | A61B 8/0825 600/440 |
| 2015/0119703 A1* | 4/2015 | Mitchell | A61B 6/5294 600/425 |
| 2015/0139520 A1* | 5/2015 | Senegas | G06T 7/0014 382/131 |
| 2015/0196228 A1* | 7/2015 | Akimoto | A61B 1/00147 600/109 |
| 2015/0297157 A1* | 10/2015 | Mukumoto | A61B 6/5205 378/15 |
| 2015/0297166 A1* | 10/2015 | Goto | G09B 23/286 378/15 |
| 2016/0007955 A1* | 1/2016 | Kuroiwa | A61B 8/06 600/441 |
| 2016/0270853 A1* | 9/2016 | Lavallee | A61F 2/461 |
| 2017/0095136 A1* | 4/2017 | Minamizato | A61B 1/00009 |
| 2017/0319164 A1* | 11/2017 | Tsukagoshi | A61B 6/469 |
| 2017/0319166 A1* | 11/2017 | Goto | A61B 6/4035 |
| 2017/0320457 A1* | 11/2017 | Kakimoto | B60H 1/00 |

FOREIGN PATENT DOCUMENTS

| | | |
|---|---|---|
| JP | 2007-167634 | 7/2007 |
| JP | 2007-181623 | 7/2007 |
| JP | 2008-6091 | 1/2008 |
| JP | 2008-11905 | 1/2008 |
| JP | 2008-12171 | 1/2008 |
| JP | 2009-142300 | 7/2009 |
| JP | 2014-188220 | 10/2014 |
| JP | 2015-213748 | 12/2015 |
| JP | 2015-213749 | 12/2015 |
| WO | WO 2007/061099 A1 | 5/2007 |

OTHER PUBLICATIONS

Japanese Office Action dated Apr. 27, 2021, issued in Japanese Patent Application No. 2017-093415.

* cited by examiner

FIG.5

| IDENTIFICATION CODE | COORDINATES | | |
|---|---|---|---|
| | POSITION DETERMINING | SCANS | |
| | | NON-CONTRAST-ENHANCED PHASE | CONTRAST-ENHANCED PHASE |
| C1 | (x1, y1, z1) | (x'1, y'1, z'1) | (x'1, y'1, z'1) |
| C2 | (x2, y2, z2) | (x'2, y'2, z'2) | (x'2, y'2, z'2) |
| C3 | (x3, y3, z3) | (x'3, y'3, z'3) | (x'3, y'3, z'3) |
| C4 | (x4, y4, z4) | (x'4, y'4, z'4) | (x'4, y'4, z'4) |
| C5 | (x5, y5, z5) | (x'5, y'5, z'5) | (x'5, y'5, z'5) |
| C6 | (x6, y6, z6) | (x'6, y'6, z'6) | (x'6, y'6, z'6) |
| C7 | (x7, y7, z7) | (x'7, y'7, z'7) | (x'7, y'7, z'7) |
| C8 | (x8, y8, z8) | (x'8, y'8, z'8) | (x'8, y'8, z'8) |
| C9 | (x9, y9, z9) | (x'9, y'9, z'9) | (x'9, y'9, z'9) |
| C10 | (x10, y10, z10) | (x'10, y'10, z'10) | (x'10, y'10, z'10) |
| ⋮ | ⋮ | ⋮ | ⋮ |
| C31 | | | (x'31, y'31, z'31) |
| C32 | | | (x'32, y'32, z'32) |
| C33 | | | (x'33, y'33, z'33) |
| C34 | | | (x'34, y'34, z'34) |
| ⋮ | ⋮ | ⋮ | ⋮ |

| LANDMARK | ABSOLUTE POSITION |
|---|---|
| C11 | 0 |
| C1 | 400 |
| C2 | 600 |

| LANDMARK | ABSOLUTE POSITION |
|---|---|
| C11 | 0 |
| C1 | 400 |
| C2 | 600 |

| LANDMARK | ABSOLUTE POSITION |
|---|---|
| C11 | 0 |
| C1 | 410 |
| C2 | 630 |

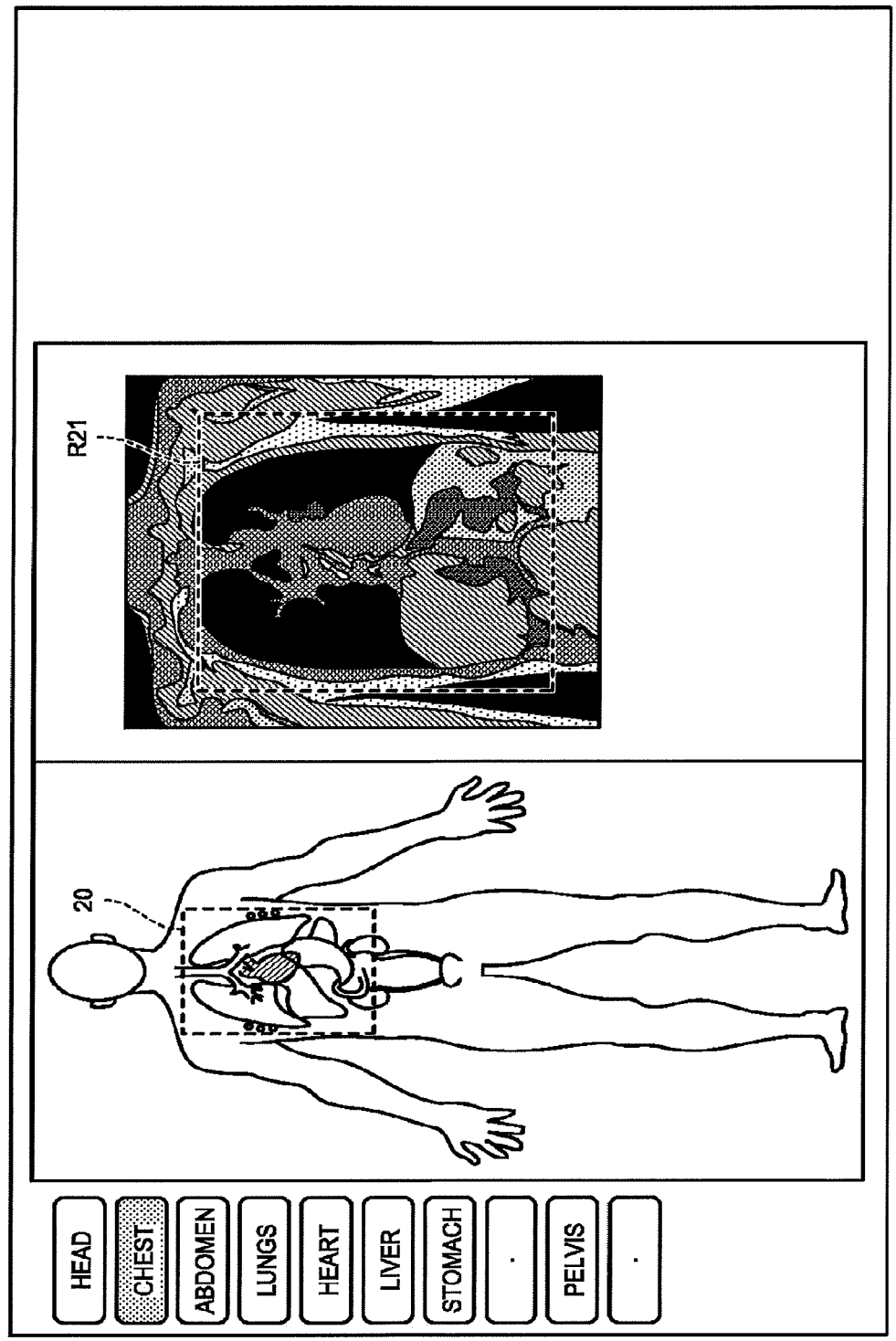

MEDICAL IMAGE DIAGNOSIS APPARATUS

CROSS-REFERENCE TO RELATED APPLICATIONS

This application is a continuation of PCT International Application No. PCT/JP2017/017605 filed on May 9, 2017 which claims the benefit of priority from Japanese Patent Application No. 2016-094082 filed on May 9, 2016, the entire contents of which are incorporated herein by reference.

FIELD

Embodiments described herein relate generally to a medical image diagnosis apparatus.

BACKGROUND

Conventionally, to perform a medical examination using a medical image diagnosis apparatus such as an X-ray Computed Tomography (CT) apparatus, a scan range is set in accordance with a scanned site. Further, such a scan range is set every time a medical examination is performed.

BRIEF DESCRIPTION OF THE DRAWINGS

FIG. 5 is a drawing for explaining another example of the site detecting process performed by the detecting function according to the first embodiment;

FIG. 20 is a drawing for explaining a fourth embodiment.

DETAILED DESCRIPTION

Exemplary embodiments of a medical image diagnosis apparatus will be explained in detail, with reference to the accompanying drawings. In the following sections, a medical information processing system that includes an X-ray Computed Tomography (CT) apparatus as a medical image diagnosis apparatus will be explained as an example. In a medical information processing system 100 in FIG. 1, although only one server apparatus and one terminal apparatus are illustrated, one or more server apparatuses and terminal apparatuses may additionally be included in actuality. Further, the medical information processing system 100 may include, for example, a medical image diagnosis apparatus such as an X-ray diagnosis apparatus, a Magnetic Resonance Imaging (MRI) apparatus, or an ultrasound diagnosis apparatus. Furthermore, in principle, the explanation of each of the embodiments is similarly applicable to any other embodiments.

A medical image diagnosis apparatus according to an embodiment includes setting circuitry and image generating circuitry. The setting circuitry is configured to obtain position information with respect to a landmark of a patient in a first image generated by performing a first scan on the patient and to set a scan range to be used during a second scan by using the obtained position information, the position information being determined on a basis of the first image and expressed in an image taking system used during the first scan. The image generating circuitry is configured to generate a second image by performing the second scan on the scan range.

First Embodiment

Figure 1:
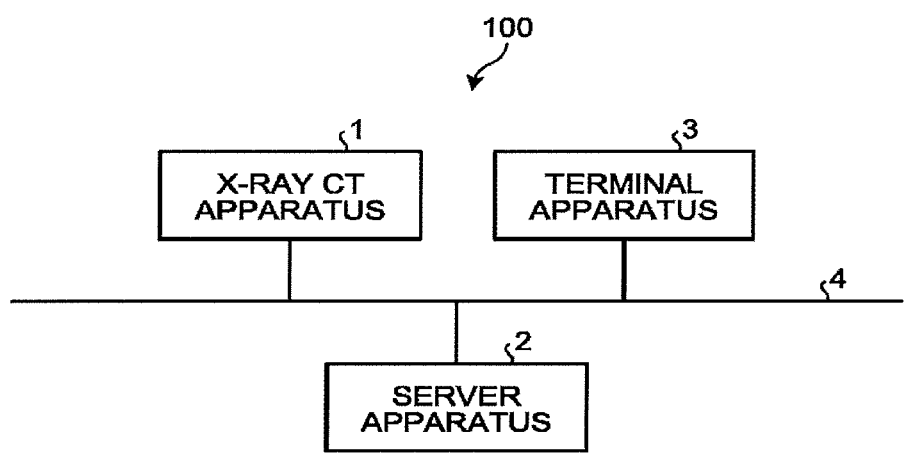
FIG. 1 is a diagram illustrating an exemplary configuration of a medical information processing system according to a first embodiment.

FIG. 1 is a diagram illustrating an exemplary configuration of the medical information processing system 100 according to a first embodiment. As illustrated in FIG. 1, the medical information processing system 100 according to the first embodiment includes an X-ray CT apparatus 1, a server apparatus 2, and a terminal apparatus 3. The X-ray CT apparatus 1, the server apparatus 2, and the terminal apparatus 3 are in a state of being able to communicate with one another either directly or indirectly via, for example, an intra-hospital Local Area Network (LAN) 4 installed in a hospital. For example, when a Picture Archiving and Communication System (PACS) is introduced into the medical information processing system 100, these apparatuses are configured to transmit and receive medical images and the like to and from one another according to the Digital Imaging and Communications in Medicine (DICOM) standard.

Further, a Hospital Information System (HIS) or a Radiology Information System (RIS), for example, is introduced into the medical information processing system 100 so as to manage various types of information. For example, the terminal apparatus 3 transmits a medical examination order generated in accordance with the system described above, to the X-ray CT apparatus 1 and to the server apparatus 2. The X-ray CT apparatus 1 obtains patient information either from the medical examination order directly received from the terminal apparatus 3 or from a patient list (a modality work list) generated in correspondence with each modality by the server apparatus 2 that received the medical examination order. The X-ray CT apparatus 1 further acquires X-ray CT image data from each patient. After that, the X-ray CT apparatus 1 transmits the acquired X-ray CT image data and image data generated by performing any of various types of image processing processes on the X-ray CT image data, to the server apparatus 2. The server apparatus 2 stores therein the X-ray CT image data and the image data received from the X-ray CT apparatus 1, and also, generates image data from the X-ray CT image data, and transmits any of the image data to the terminal apparatus 3 in response to an obtainment request from the terminal apparatus 3. The terminal apparatus 3 displays the image data received from the server apparatus 2 on a monitor or the like. The following sections describe each of the apparatuses.

The terminal apparatus 3 is an apparatus provided in each medical department in the hospital and is operated by medical doctors working in various medical departments. The terminal apparatus 3 may be a Personal Computer (PC), a tablet-type PC, a Personal Digital Assistant (PDA), a mobile phone, or the like. For example, to the terminal apparatus 3, medical doctors input medical chart information including patients' symptoms and medical doctors' observations. Further, to the terminal apparatus 3, a medical examination order that orders a medical examination to be performed by the X-ray CT apparatus 1 is input. The terminal apparatus 3 transmits the input medical examination order to the X-ray CT apparatus 1 and to the server apparatus 2. In other words, each of the medical doctors working in the medical departments operates the terminal apparatus 3 so as to read reception information and electronic chart information of each patient who came to the hospital, gives a consultation to his/her patient, and inputs medical chart information to a read electronic chart. After that, each of the medical doctors working in the medical departments transmits the medical examination order by operating the terminal apparatus 3, depending on whether or not a medical examination using the X-ray CT apparatus 1 is required.

The server apparatus 2 is an apparatus configured to store therein medical images acquired by a medical image diagnosis apparatus (e.g., the X-ray CT image data and the image data acquired by the X-ray CT apparatus 1) and to perform various types of image processing processes on the medical images. For example, the server apparatus 2 may be configured by using a PACS server. For example, the server apparatus 2 is configured to receive a plurality of medical examination orders from the terminal apparatus 3 provided in each of the medical departments, to generate a patient list for each medical image diagnosis apparatus, and to transmit each of the generated patient lists to a corresponding one of the medical image diagnosis apparatuses. In one example, the server apparatus 2 receives medical examination orders for performing medical examinations by using the X-ray CT apparatus 1 from the terminal apparatus 3 provided in each medical department, generates the patient lists, and transmits a corresponding one of the generated patient lists to the X-ray CT apparatus 1. After that, the server apparatus 2 stores therein the X-ray CT image data and the image data acquired by the X-ray CT apparatus 1 and further transmits the X-ray CT image data and the image data to the terminal apparatus 3, in response to an obtainment request from the terminal apparatus 3. Further, the server apparatus 2 stores therein a medical examination history from the past. For example, as the medical examination history, the server apparatus 2 stores therein image taking conditions such as scan ranges and reconstruction conditions of image data, so as to be kept in correspondence with patient identifiers (IDs).

Figure 2:
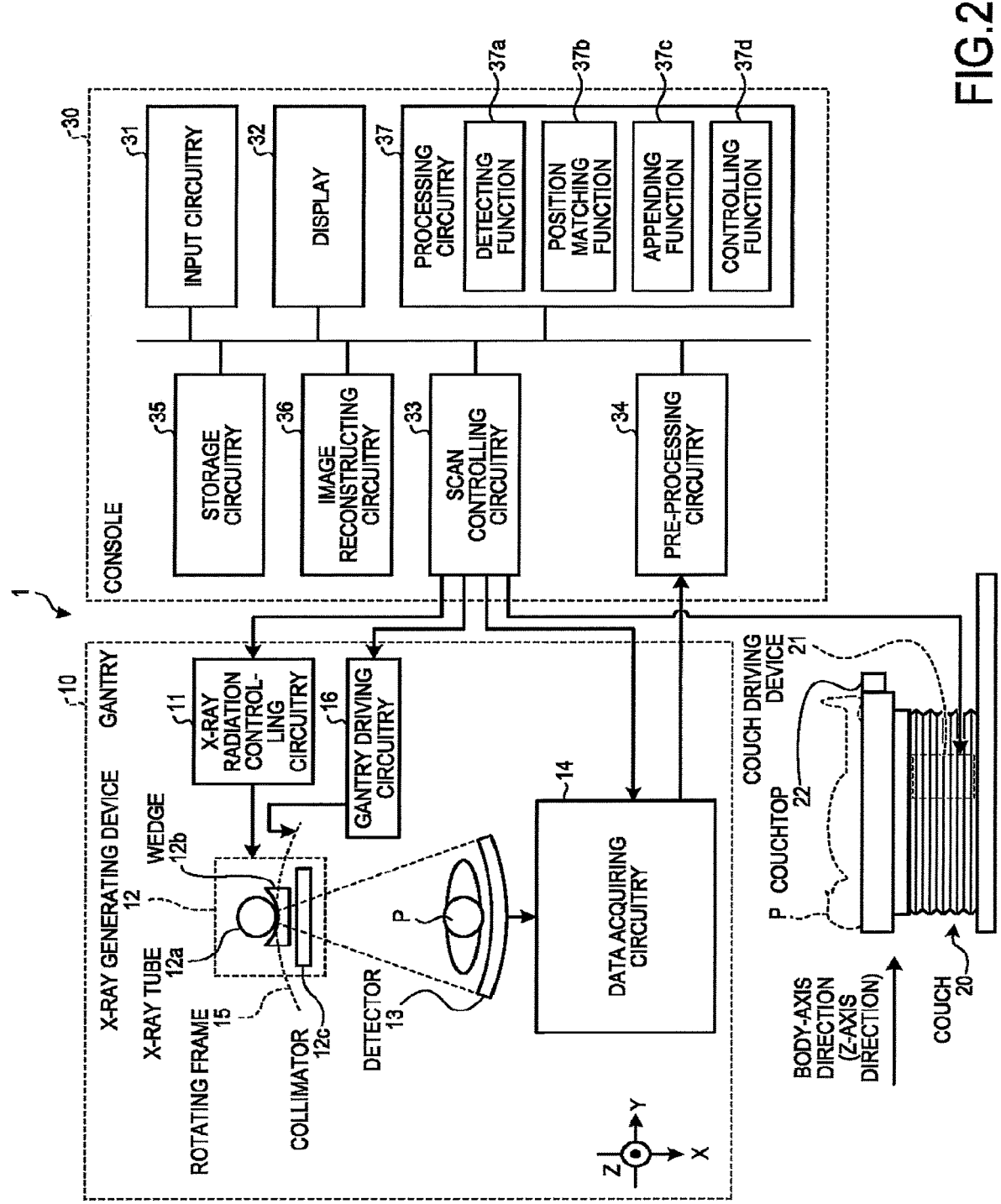
FIG. 2 is a diagram illustrating an exemplary configuration of an X-ray CT apparatus according to the first embodiment.

The X-ray CT apparatus 1 is configured to acquire the X-ray CT image data from each patient and to transmit the acquired X-ray CT image data and the image data generated by performing any of the various types of image processing processes on the X-ray CT image data, to the server apparatus 2. FIG. 2 is a diagram illustrating an exemplary configuration of the X-ray CT apparatus 1 according to the first embodiment. As illustrated in FIG. 2, the X-ray CT apparatus 1 according to the first embodiment includes a gantry 10, a couch 20, and a console 30. Further, the X-ray CT apparatus 1 is connected to a contrast agent injector (not illustrated in FIG. 2).

The gantry 10 is a device configured to radiate X-rays onto an examined subject P (the patient), to detect X-rays that have passed through the patient P, and to output a result of the detection to the console 30. The gantry 10 includes X-ray radiation controlling circuitry 11, an X-ray generating device 12, a detector 13, and data acquiring circuitry (a Data Acquisition System [DAS]) 14, a rotating frame 15, and gantry driving circuitry 16.

The rotating frame 15 is an annular frame configured to support the X-ray generating device 12 and the detector 13 so as to oppose each other while the patient P is interposed therebetween and configured to be rotated by the gantry driving circuitry 16 (explained later) at a high speed on a circular orbit centered on the patient P.

The X-ray radiation controlling circuitry 11 is a device configured, as a high-voltage generating unit, to supply a high voltage to an X-ray tube 12*a*. The X-ray tube 12*a* is configured to generate X-rays by using the high voltage supplied thereto from the X-ray radiation controlling circuitry 11. The X-ray radiation controlling circuitry 11 is configured to adjust the X-ray dose radiated onto the patient P, by adjusting the X-ray tube voltage and the X-ray tube current supplied to the X-ray tube 12*a*, under control of scan controlling circuitry 33 (explained later).

Further, the X-ray radiation controlling circuitry 11 is configured to perform a switching process on a wedge 12*b*. Further, by adjusting the opening degree of a collimator 12*c*, the X-ray radiation controlling circuitry 11 is configured to adjust the radiation range (a fan angle and a cone angle) of the X-rays. In the present embodiments, an arrangement is acceptable in which an operator manually switches among a plurality of types of wedges.

The X-ray generating device 12 is a device configured to generate the X-rays and to radiate the generated X-rays onto the patient P. The X-ray generating device 12 includes the X-ray tube 12*a*, the wedge 12*b*, and the collimator 12*c*.

The X-ray tube 12*a* is a vacuum tube configured to radiate an X-ray beam onto the patient P by using the high voltage supplied thereto by the high-voltage generating unit (not illustrated). The X-ray tube 12*a* radiates the X-ray beam onto the patient P, as the rotating frame 15 rotates. The X-ray tube 12*a* is configured to generate the X-ray beam that spreads with the fan angle and the cone angle. For example, under the control of the X-ray radiation controlling circuitry 11, the X-ray tube 12a is capable of continuously emitting X-rays in the entire surrounding of the patient P to realize a full reconstruction process and is capable of continuously emitting X-rays in an emission range (180 degrees+the fan angle) that enables a half reconstruction to realize a half reconstruction process. Further, under the control of the X-ray radiation controlling circuitry 11, the X-ray tube 12a is capable of intermittently emitting X-rays (pulse X-rays) in positions (X-ray tube positions) set in advance. Further, the X-ray radiation controlling circuitry 11 is also capable of modulating the intensities of the X-rays emitted from the X-ray tube 12a. For example, the X-ray radiation controlling circuitry 11 increases the intensities of the X-rays emitted from the X-ray tube 12a in a specific X-ray tube position and decreases the intensities of the X-rays emitted from the X-ray tube 12a in a range other than the specific X-ray tube position.

The wedge 12b is an X-ray filter configured to adjust the X-ray dose of the X-rays emitted from the X-ray tube 12a. More specifically, the wedge 12b is a filter configured to pass and attenuate the X-rays emitted from the X-ray tube 12a, so that the X-rays radiated from the X-ray tube 12a onto the patient P have a predetermined distribution. For example, the wedge 12b is a filter obtained by processing aluminum so as to have a predetermined target angle and a predetermined thickness. The wedge may be referred to as a wedge filter or a bow-tie filter.

The collimator 12c is a slit configured to narrow down the radiation range of the X-rays of which the X-ray dose has been adjusted by the wedge 12b, under the control of the X-ray radiation controlling circuitry 11 (explained later).

The gantry driving circuitry 16 is configured to cause the X-ray generating device 12 and the detector 13 to revolve on the circular orbit centered on the patient P, by driving the rotating frame 15 to rotate.

The detector 13 is a two-dimensional array detector (a planar detector) configured to detect the X-rays that have passed through the patient P. In the detector 13, a plurality of rows of detecting elements is arranged along the body-axis direction of the patient P (i.e., the Z-axis direction in FIG. 2), while each row contains a plurality of X-ray detecting elements corresponding to a plurality of channels. More specifically, the detector 13 according to the first embodiment includes the X-ray detecting elements that are arranged in a large number of rows (e.g., 320 rows) along the body-axis direction of the patient P. For example, the detector 13 is capable of detecting X-rays that have passed through the patient P in a wide range such as a range including the lungs or the heart of the patient P.

The data acquiring circuitry 14 is configured with the DAS and is configured to acquire projection data from X-ray detection data detected by the detector 13. For example, the data acquiring circuitry 14 generates the projection data by performing an amplifying process, an Analog/Digital (A/D) converting process, a sensitivity correcting process among the channels, and/or the like on X-ray intensity distribution data detected by the detector 13 and further transmits the generated projection data to the console 30 (explained later). For example, when X-rays are continuously emitted from the X-ray tube 12a while the rotating frame 15 is rotating, the data acquiring circuitry 14 acquires a group of projection data corresponding to the entire surrounding (corresponding to 360 degrees). Further, the data acquiring circuitry 14 transmits the acquired pieces of projection data to the console 30 (explained later), while keeping the pieces of projection data in correspondence with the X-ray tube positions. The X-ray tube positions serve as information indicating projection directions of the pieces of projection data. Alternatively, the sensitivity correcting process among the channels may be performed by pre-processing circuitry 34 (explained later).

The couch 20 is a device on which the patient P is placed and includes a couch driving device 21 and a couchtop 22, as illustrated in FIG. 2. The couch driving device 21 is configured to move the patient P into the rotating frame 15 by moving the couchtop 22 in the Z-axis direction. The couchtop 22 is a board on which the patient P is placed.

For example, the gantry 10 performs a helical scan by which the patient P is helically scanned by causing the rotating frame 15 to rotate while the couchtop 22 is being moved. In another example, the gantry 10 performs a conventional scan by which the patient P is scanned on a circular orbit by causing the rotating frame 15 to rotate, while the position of the patient P is being fixed after the couchtop 22 is moved. In yet another example, the gantry 10 implements a step-and-shoot method by which the conventional scan is performed in multiple scan areas, by moving the position of the couchtop 22 at regular intervals.

The console 30 is a device configured to receive operations performed by the operator on the X-ray CT apparatus 1 and also configured to reconstruct X-ray CT image data by using the projection data acquired by the gantry 10. As illustrated in FIG. 2, the console 30 includes input circuitry 31, a display 32, the scan controlling circuitry 33, the pre-processing circuitry 34, storage circuitry 35, image reconstructing circuitry 36, and processing circuitry 37.

The input circuitry 31 includes a mouse, a keyboard, a trackball, a switch, a button, a joystick, and/or the like used by the operator of the X-ray CT apparatus 1 to input various types of instructions and various types of settings. The input circuitry 31 is configured to transfer information about the instructions and the settings received from the operator to the processing circuitry 37. For example, the input circuitry 31 receives, from the operator, an image taking condition for the X-ray CT image data, a reconstruction condition used when the X-ray CT image data is reconstructed, an image processing condition applied to the X-ray CT image data, and the like. Further, the input circuitry 31 also receives an operation to select a medical examination to be performed on the patient P. In addition, the input circuitry 31 receives a designation operation to designate a site rendered in an image.

The display 32 is a monitor referenced by the operator and is configured to display the image data generated from the X-ray CT image data for the operator and to display a Graphical User Interface (GUI) used for receiving the various types of instructions and the various types of settings from the operator via the input circuitry 31, under control of the processing circuitry 37. Further, the display 32 is also configured to display a planning screen for a scan plan and a screen of images during a scan. Further, the display 32 is configured to display a virtual patient image, image data, or the like including radiation exposure information. The virtual patient image displayed by the display 32 will be explained in detail later.

Under the control of the processing circuitry 37, the scan controlling circuitry 33 is configured to control the projection data acquiring process performed by the gantry 10, by controlling operations of the X-ray radiation controlling circuitry 11, the gantry driving circuitry 16, the data acquiring circuitry 14, and the couch driving device 21. More specifically, the scan controlling circuitry 33 is configured to control projection data acquiring processes during an image taking process to acquire a position determining image (a scanogram image) and during a main image taking process (a scan) to acquire an image used for a diagnosis purpose. In the present example, the X-ray CT apparatus 1 according to the first embodiment is configured so as to be able to take a two-dimensional scanogram image and a three-dimensional scanogram image.

For example, by continuously taking images while moving the couchtop 22 at a constant speed and having the X-ray tube 12a fixed in the position corresponding to 0 degrees (a straight-on position of the patient P), the scan controlling circuitry 33 takes the two-dimensional scanogram image. Alternatively, by intermittently moving the couchtop 22 while the X-ray tube 12a is fixed in the position corresponding to 0 degrees, the scan controlling circuitry 33 may take the two-dimensional scanogram image by repeatedly taking images intermittently in synchronization with the moving of the couchtop. In the present example, the scan controlling circuitry 33 is capable of taking the position determining image, not only from the straight-on direction of the patient P, but also from any arbitrary direction (e.g., a lateral direction).

Figure 3:
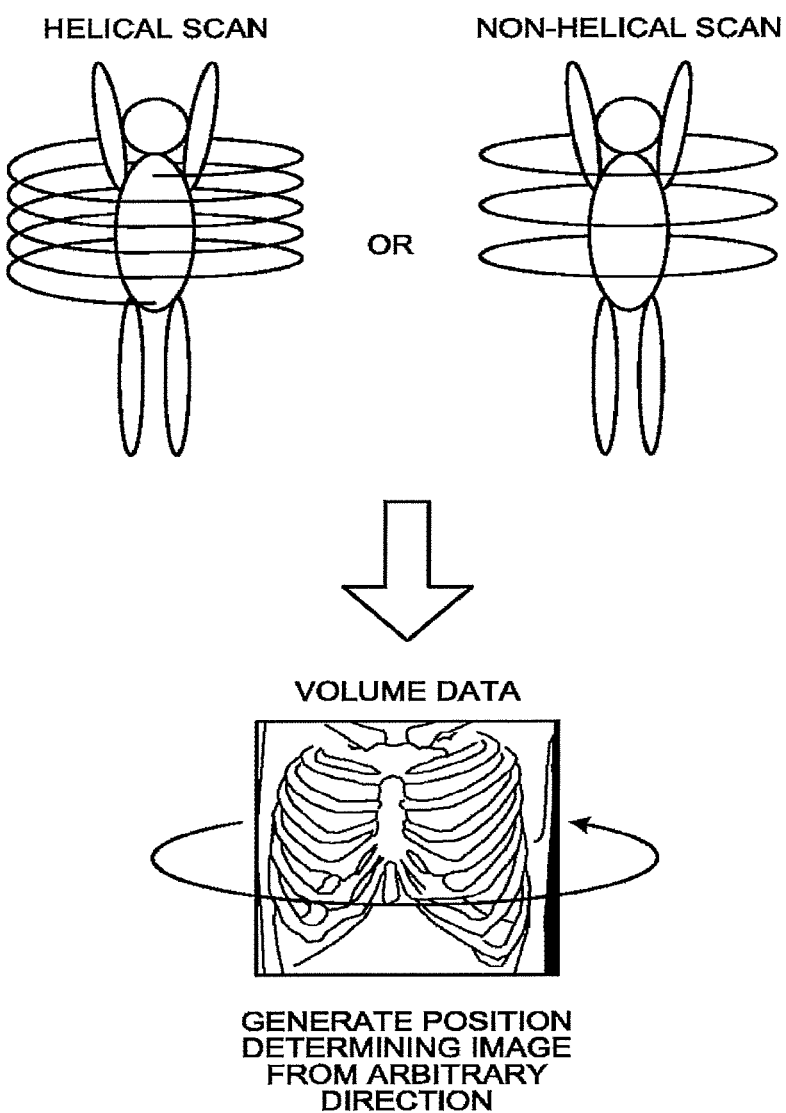
FIG. 3 is a drawing for explaining a three-dimensional scanogram image taking process performed by scan controlling circuitry according to the first embodiment.

Further, by acquiring the projection data corresponding to the entire surrounding of the patient P during a scanogram image taking process, the scan controlling circuitry 33 takes the three-dimensional scanogram image. FIG. 3 is a drawing for explaining a three-dimensional scanogram image taking process performed by the scan controlling circuitry 33 according to the first embodiment. For example, as illustrated in FIG. 3, the scan controlling circuitry 33 acquires the projection data corresponding to the entire surrounding of the patient P, by performing either a helical scan or a non-helical scan. In this situation, the scan controlling circuitry 33 performs the helical scan or the non-helical scan on a wide range such as the entire chest, the entire abdomen, the entire upper body, or the entire body of the patient P, by using a radiation dose smaller than that used in the main image taking process. To perform the non-helical scan, for example, a scan is performed by implementing the step-and-shoot method described above.

When the scan controlling circuitry 33 has acquired the projection data corresponding to the entire surrounding of the patient P in this manner, the image reconstructing circuitry 36 (explained later) is able to reconstruct three-dimensional X-ray CT image data (volume data), and it is therefore possible to generate a position determining image from an arbitrary direction, by using the reconstructed volume data, as illustrated in FIG. 3. In this situation, whether the position determining image is taken two-dimensionally or three-dimensionally may arbitrarily be set by the operator or may be set in advance in accordance with specifics of the medical examination.

Returning to the description of FIG. 2, the pre-processing circuitry 34 is configured to generate corrected projection data by performing a logarithmic converting process as well as correcting processes such as an offset correcting process, a sensitivity correcting process, a beam hardening correcting process, and the like, on the projection data generated by the data acquiring circuitry 14. More specifically, the pre-processing circuitry 34 generates pieces of corrected projection data both for the projection data of the position determining image and for the projection data acquired by performing the main image taking process that were generated by the data acquiring circuitry 14 and further stores the pieces of corrected projection data into the storage circuitry 35.

The storage circuitry 35 is configured to store therein the projection data generated by the pre-processing circuitry 34. More specifically, the storage circuitry 35 stores therein the projection data of the position determining image and the projection data for the diagnosis purpose acquired by performing the main image taking process that were generated by the pre-processing circuitry 34. Further, the storage circuitry 35 is configured to store therein image data generated by the image reconstructing circuitry 36 (explained later), the virtual patient image, and the like. Further, the storage circuitry 35 is configured to store therein a processing result obtained by the processing circuitry 37 (explained later), as appropriate. The virtual patient image and the processing result obtained by the processing circuitry 37 will be explained later.

The image reconstructing circuitry 36 is configured to reconstruct the X-ray CT image data by using the projection data stored in the storage circuitry 35. More specifically, the image reconstructing circuitry 36 reconstructs pieces of X-ray CT image data both from the projection data of the position determining image and from the projection data of the image for the diagnosis purpose. In this situation, any of various methods can be used as the reconstructing method. For example, a back projection process may be used. Further, examples of the back projection process include a back projection process using a Filtered Back Projection (FBP) method. Alternatively, the image reconstructing circuitry 36 may reconstruct the X-ray CT image data by using a successive approximation method. The image reconstructing circuitry 36 may also be referred to as image generating circuitry.

Further, the image reconstructing circuitry 36 is configured to generate image data by performing various types of image processing processes on the X-ray CT image data. After that, the image reconstructing circuitry 36 stores the reconstructed X-ray CT image data and the image data generated by performing the various types of image processing processes, into the storage circuitry 35.

The processing circuitry 37 is configured to exercise overall control of the X-ray CT apparatus 1 by controlling operations of the gantry 10, the couch 20, and the console 30. More specifically, the processing circuitry 37 is configured to control a CT scan performed by the gantry 10, by controlling the scan controlling circuitry 33. Also, the processing circuitry 37 is configured to control the image reconstruction process and the image generating process performed by the console 30, by controlling the image reconstructing circuitry 36. Further, the processing circuitry 37 is configured to exercise control so that the display 32 displays any of the various types of image data stored in the storage circuitry 35.

Further, as illustrated in FIG. 2, the processing circuitry 37 is configured to execute a detecting function 37a, a position matching function 37b, an appending function 37c, and a controlling function 37d. In this situation, for example, processing functions executed by the constituent elements of the processing circuitry 37 illustrated in FIG. 2, namely the functions such as the detecting function 37a, the position matching function 37b, the appending function 37c, and the controlling function 37d are recorded in the storage circuitry 35 in the form of computer-executable programs. The processing circuitry 37 is a processor configured to realize the functions corresponding to the computer programs (hereinafter, "programs"), by reading the programs from the storage circuitry 35 and executing the read programs. In other words, the processing circuitry 37 that has read the programs has the functions illustrated within the processing circuitry 37 in FIG. 2. The detecting function 37a may also be referred to as detecting circuitry. The appending function 37c may also be referred to as generating circuitry. The controlling function 37d may also be referred to as setting circuitry.

The detecting function 37a is configured to detect each of a plurality of sites of the patient P included in the three-dimensional image data. More specifically, the detecting function 37a detects each of the sites such as the organs included in the three-dimensional X-ray CT image data (the volume data) reconstructed by the image reconstructing circuitry 36. For example, with respect to at least one selected from between the volume data of the position determining image and the volume data of the image for the diagnosis purpose, the detecting function 37a performs an Anatomical Landmark (AL) analysis by detecting the sites such as the organs on the basis of anatomical feature points called anatomical landmarks. In the present example, the term "anatomical landmark" denotes a point indicating a feature of a site such as a specific bone, organ, blood vessel, nerve, or lumen. In other words, by detecting the anatomical landmark of a specific organ, bone, or the like, the detecting function 37a detects the bone, organ, blood vessel, nerve, lumen, or the like included in the volume data. Further, by detecting the landmark (the feature point) characteristic to human bodies, the detecting function 37a is also capable of detecting the positions of the head, the neck, the chest, the abdomen, the feet, and/or the like included in the volume data. The "sites" used in the description of the present embodiments include any of these positions, in addition to bones, organs, blood vessels, nerves, lumens, and the like. In the following sections, an example of a site detecting process performed by the detecting function 37a will be explained. The "site detecting process" performed by the detecting function 37a may also be referred to as an "AL analysis".

For example, with respect to either the volume data of the position determining image or the volume data of the image for the diagnosis purpose, the detecting function 37a extracts the anatomical landmarks on the basis of voxel values included in the volume data. After that, the detecting function 37a optimizes the positions of the landmarks extracted from the volume data, by eliminating inaccurate landmarks from among the landmarks extracted from the volume data, by comparing the three-dimensional positions of the anatomical landmarks based on information from textbooks and the like, with the positions of the landmarks extracted from the volume data. As a result, the detecting function 37a detects various sites of the patient P included in the volume data. In one example, the detecting function 37a, at first, extracts the anatomical landmarks included in the volume data, by using a supervised machine learning algorithm. In the present example, the supervised machine learning algorithm is structured by using a plurality of teacher images in which correct anatomical landmarks are manually arranged. The supervised machine learning algorithm may be configured by using a decision forest, for example.

Further, the detecting function 37a optimizes the extracted landmarks by comparing a model indicating three-dimensional positional relationships among anatomical landmarks of human bodies with the extracted landmarks. In the present example, the model is structured by using the aforementioned teaching images and may be configured by using a point distribution model, for example. In other words, the detecting function 37a optimizes the landmarks by eliminating the inaccurate landmarks, by comparing the model with the extracted landmarks, the model defining the shapes of various sites, the positional relationships thereof, points unique to the sites, and the like on the basis of the plurality of teacher images in which the correct anatomical landmarks are manually arranged.

Figure 4A:
FIG. 4A is a drawing for explaining an example of a site detecting process performed by a detecting function according to the first embodiment.
Figure 4B:
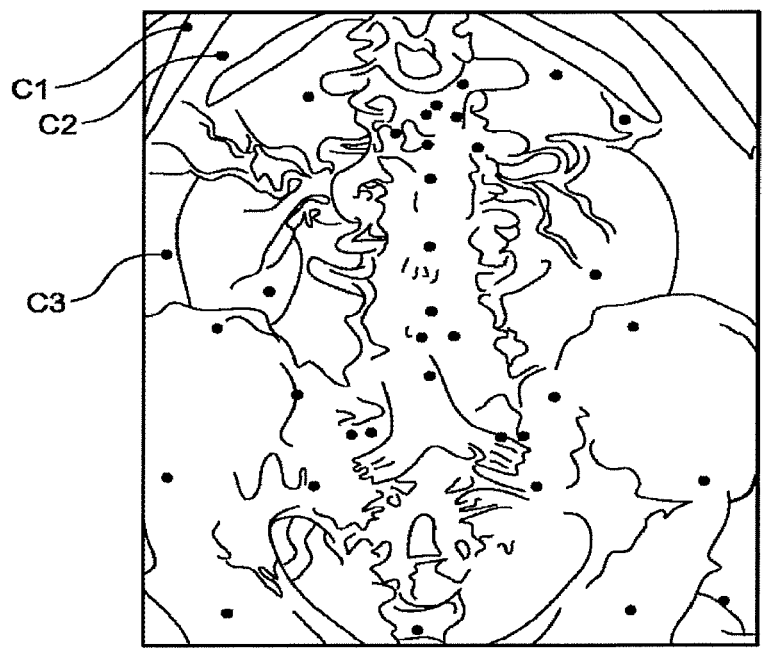
FIG. 4B is another drawing for explaining the example of the site detecting process performed by the detecting function according to the first embodiment.

Next, an example of the site detecting process performed by the detecting function 37a will be explained, with reference to FIGS. 4A, 4B, 5, and 6. FIGS. 4A, 4B, 5, and 6 are drawings for explaining examples of the site detecting process performed by the detecting function 37a according to the first embodiment. Although landmarks are arranged two-dimensionally in FIGS. 4A and 4B, the landmarks are arranged three-dimensionally in actuality. For example, by applying the supervised machine learning algorithm to the volume data, the detecting function 37a extracts voxels regarded as anatomical landmarks (the dots in the drawing), as illustrated in FIG. 4A. Further, by fitting the positions of the extracted voxels to a model defining shapes of various sites, positional relationships thereof, points unique to the sites, and the like, the detecting function 37a extracts only such voxels that correspond to more accurate landmarks, by eliminating inaccurate landmarks from among the extracted voxels, as illustrated in FIG. 4B.

In this situation, the detecting function 37a assigns identification codes for identifying the landmarks indicating the features of the sites, to the extracted landmarks (voxels) and further attaches information in which the identification codes are kept in correspondence with position (coordinates) information of the landmarks to the image data, before storing the image data into the storage circuitry 35. For example, as illustrated in FIG. 4B, the detecting function 37a assigns identification codes such as C1, C2, and C3 to the extracted landmarks (the voxels). In this situation, the detecting function 37a attaches an identification code to each of the pieces of data resulting from the detecting process, before storing the pieces of data into the storage circuitry 35. More specifically, the detecting function 37a is configured to detect sites of the patient included in the volume data reconstructed from at least one selected from among: the projection data of the position determining image; projection data acquired in a non-contrast-enhanced state; and projection data acquired while the contrast is enhanced by a contrast agent.

For example, as illustrated in FIG. 5, the detecting function 37a attaches information in which the identification codes are kept in correspondence with the coordinates of the voxels detected from the volume data of the position determining image ("position determining" in the table) to the volume data, before storing the volume data into the storage circuitry 35. In one example, the detecting function 37a extracts the coordinates of landmark points from the volume data of the position determining image and, as illustrated in FIG. 5, stores information such as "identification code: C1, coordinates $(x_1,y_1,z_1)$" and "identification code: C2, coordinates $(x_2,y_2,z_2)$" so as to be kept in correspondence with the volume data. As a result, the detecting function 37a is able to identify what landmarks are present in which positions within the volume data of the position determining image. The detecting function 37a is thus able to detect various sites such as organs on the basis of these pieces of information.

Further, as illustrated in FIG. 5, for example, the detecting function 37a attaches information in which the identification codes are kept in correspondence with the coordinates of the voxels detected from the volume data of the diagnosis-purpose image ("scans" in the table) to the volume data, before storing the volume data into the storage circuitry 35.

In this situation, during the scans, the detecting function 37a is able to extract the coordinates of the landmark points from volume data in which the contrast is enhanced by a contrast agent ("contrast-enhanced phase" in the table) and from volume data in which the contrast is not enhanced by a contrast agent ("non-contrast-enhanced phase" in the table), so as to bring the identification codes into correspondence with the extracted coordinates.

In one example, from within the volume data of the diagnosis-purpose image, the detecting function 37a extracts the coordinates of the landmark points from the volume data in the non-contrast-enhanced phase and, as illustrated in FIG. 5, brings information such as "identification code C1, coordinates $(x'_1, y'_1, z'_1)$" and "identification code C2, coordinates $(x'_2, y'_2, z'_2)$" into correspondence with the volume data, before storing the volume data. Further, from within the volume data of the diagnosis-purpose image, the detecting function 37a extracts the coordinates of the landmark points from the volume data in the contrast-enhanced phase and, as illustrated in FIG. 5, brings information such as "identification code C1, coordinates $(x'_1, y'_1, z'_1)$" and "identification code C2, coordinates $(x'_2, y'_2, z'_2)$" into correspondence with the volume data, before storing the volume data. In this situation, when the landmark points are extracted from the volume data in the contrast-enhanced phase, the landmark points include one or more landmark points that became extractable because of the contrast enhancement. For example, when extracting the landmark points from the volume data in the contrast-enhanced phase, the detecting function 37a is able to extract blood vessels and the like of which the contrast was enhanced by the contrast agent. Accordingly, for the volume data in the contrast-enhanced phase, as illustrated in FIG. 5, the detecting function 37a brings identification codes C31, C32, C33, and C34 each of which is used for identifying a different one of blood vessels, into correspondence with the coordinates such as $(x'_{31}, y'_{31}, z'_{31})$ to $(x'_{34}, y'_{34}, z'_{34})$ of the landmark points represented by the blood vessels and the like that were extracted as a result of the contrast enhancement.

As explained above, the detecting function 37a is able to identify what landmark points are present in which positions within the volume data of the position determining image and within the volume data of the diagnosis-purpose image. The detecting function 37a is thus able to detect various sites such as organs on the basis of these pieces of information. For example, by using information about an anatomical positional relationship between a target site subject to the detection and other sites positioned in the surroundings of the target site, the detecting function 37a detects the position of the target site. In one example, when the target site is the "lungs", the detecting function 37a obtains coordinate information kept in correspondence with identification codes indicating features of the lungs and further obtains coordinate information kept in correspondence with identification codes indicating sites positioned in the surroundings of the "lungs", such as the "ribs", the "clavicles", the "heart", the "diaphragm", and so on. Further, the detecting function 37a extracts a region of the "lungs" in the volume data by using information about an anatomical positional relationship between the "lungs" and the sites in the surroundings thereof and the obtained coordinate information.

Figure 6:
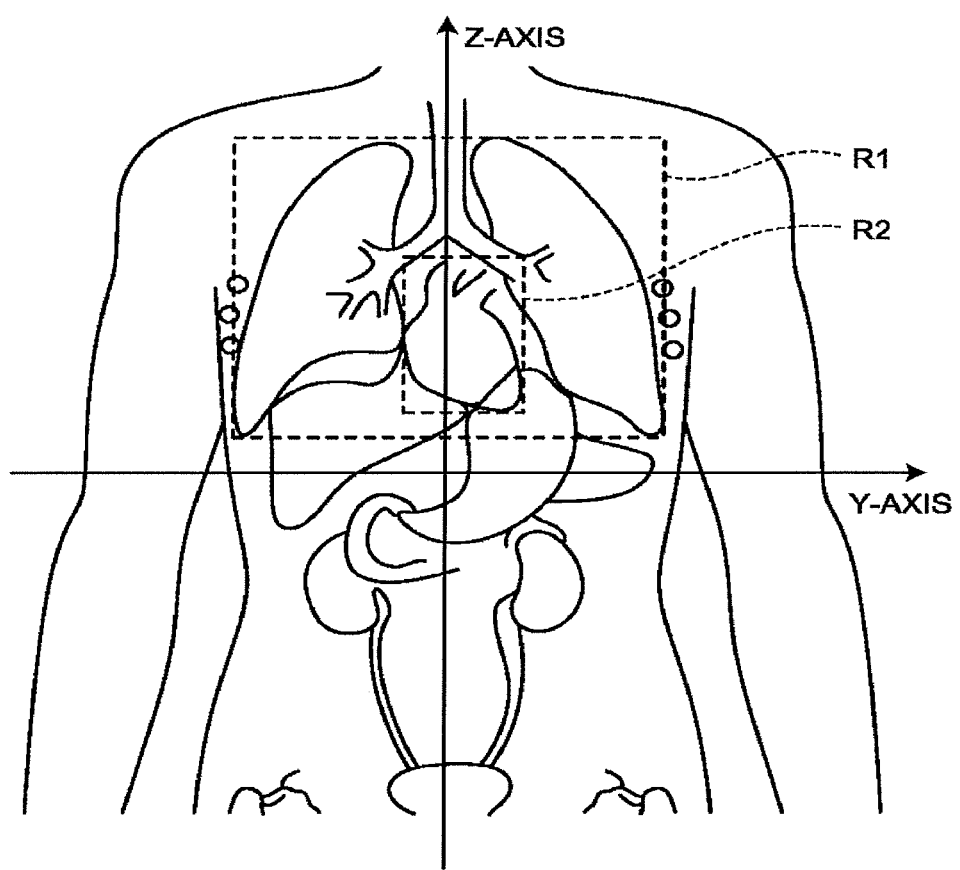
FIG. 6 is a drawing for explaining yet another example of the site detecting process performed by the detecting function according to the first embodiment.

For example, the detecting function 37a extracts a region R1 corresponding to the "lungs" in the volume data, as illustrated in FIG. 6, on the basis of information about positional relationships such as "the lung apices: 2 to 3 cm above the clavicles" and "the lower ends of the lungs: at the height of the seventh ribs", as well as the coordinate information of the sites. In other words, the detecting function 37a extracts the coordinate information of the voxels in the region R1 within the volume data. The detecting function 37a brings the extracted coordinate information into correspondence with site information and further attaches these pieces of information to the volume data, before storing the volume data into the storage circuitry 35. Similarly, as illustrated in FIG. 6, the detecting function 37a is also able to extract a region R2 corresponding to the "heart" in the volume data.

Further, on the basis of landmarks defining the positions of the head, the chest, and the like in the human body, the detecting function 37a detects positions included in the volume data. In this situation, it is possible to arbitrarily define the positions of the head, the chest, and the like in the human body. For example, when the region from the seventh cervical vertebra to the lower ends of the lungs are defined as the chest, the detecting function 37a detects a region from a landmark corresponding to the seventh cervical vertebra to a landmark corresponding to the lower ends of the lungs as the chest. In this situation, the detecting function 37a is capable of detecting sites by using other various methods besides the abovementioned method using the anatomical landmarks. For example, the detecting function 37a is capable of detecting the sites included in the volume data by implementing a region growing method based on voxel values, or the like.

The position matching function 37b is configured to match the position of each of the plurality of sites of the patient P included in the three-dimensional image data with the position of each of a plurality of sites in a human body included in virtual patient data. In this situation, the virtual patient data is information indicating a standard position of each of a plurality of sites in the human body. In other words, the position matching function 37b matches the sites of the patient P with the standard positions of the sites and further stores a matching result into the storage circuitry 35. For example, the position matching function 37b matches the virtual patient image in which sites in the human body are arranged in standard positions, with the volume data of the patient P.

Next, the virtual patient image will be explained first. The virtual patient image is generated in advance and stored in the storage circuitry 35 as an image actually taken of a human body by using X-rays, the human body having a standard physique corresponding to a plurality of combinations related to parameters with regard to physiques such as the age, adult/child, male/female, the weight, and the height. In other words, the storage circuitry 35 stores therein data of a plurality of virtual patient images corresponding to the different combinations of the parameters presented above. In this situation, the virtual patient images stored in the storage circuitry 35 are stored while being kept in correspondence with anatomical landmarks (landmarks). For example, the human body has a large number of anatomical landmarks that can be extracted from images relatively easily on the basis of morphological features thereof or the like, by performing an image processing process such as a pattern recognition process. The positions and positional arrangements of the large number of anatomical landmarks in human bodies are roughly fixed depending on physiques corresponding to ages, adult/child, male/female, the weights, and the heights.

Figure 7:
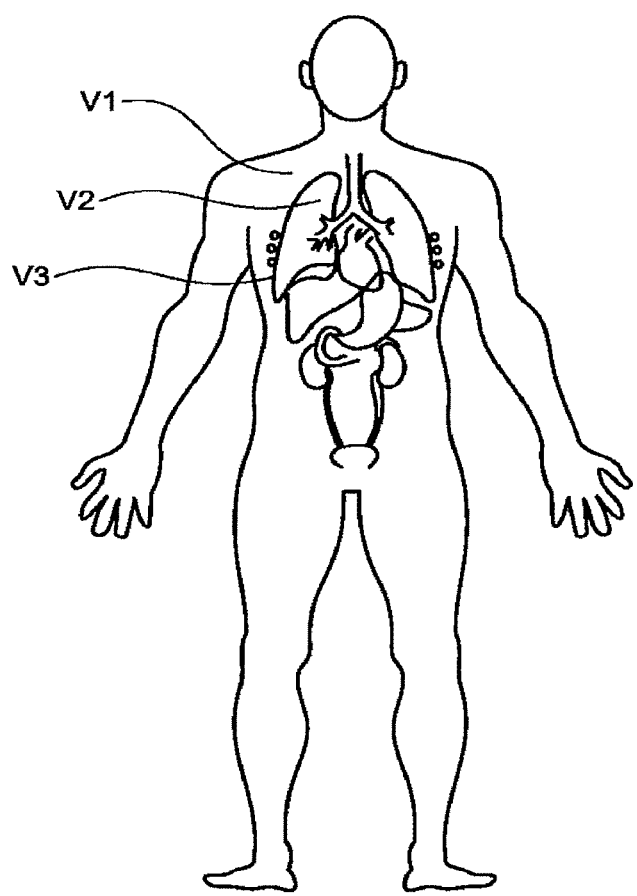
FIG. 7 is a drawing illustrating an example of a virtual patient image stored in storage circuitry according to the first embodiment.

The virtual patient images stored in the storage circuitry 35 are stored after the large number of anatomical landmarks are detected in advance, and position data of the detected landmarks is either attached to or associated with the data of the virtual patient images, together with the respective identification codes of the landmarks. FIG. 7 is a drawing illustrating an example of the virtual patient images stored in the storage circuitry 35 according to the first embodiment. For example, as illustrated in FIG. 7, the storage circuitry 35 stores therein a virtual patient image in which anatomical landmarks and identification codes such as "V1", "V2", "V3", and so on used for identifying the landmarks are kept in association with a three-dimensional human body including sites such as organs.

In other words, the storage circuitry 35 stores therein the coordinates of the landmarks within a coordinate space of a three-dimensional human body image so as to be kept in association with the corresponding identification codes. In one example, the storage circuitry 35 stores therein the coordinates of the corresponding landmark so as to be kept in correspondence with the identification code "V1" illustrated in FIG. 7. Similarly, the storage circuitry 35 stores therein the identification codes and the coordinates of the landmarks so as to be kept in correspondence with one another. Although FIG. 7 illustrates only the lungs, the heart, the liver, the stomach, and the kidneys as organs, the virtual patient image in actuality further includes a large number of organs, bonds, blood vessels, nerves, and the like. Further, although FIG. 7 illustrates only the landmarks corresponding to the identification codes "V1", "V2", and "V3", the virtual patient image in actuality further includes a larger number of landmarks.

Figure 8:
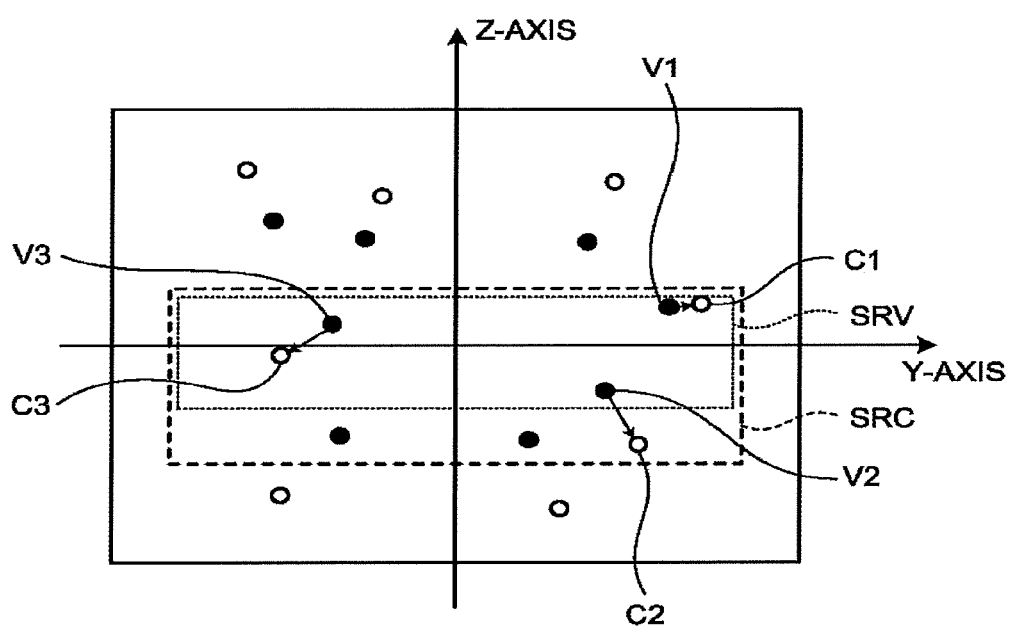
FIG. 8 is a drawing for explaining an example of a matching process performed by a position matching function according to the first embodiment.

The position matching function 37b brings the coordinate space of the volume data into association with the coordinate space of the virtual patient image, by matching the landmarks in the volume data of the patient P detected by the detecting function 37a with the landmarks in the abovementioned virtual patient image, by using the identification codes. FIG. 8 is a drawing for explaining an example of the matching process performed by the position matching function 37b according to the first embodiment. In this situation, FIG. 8 illustrates an example in which the matching process is performed by using three sets of landmarks to which identification codes are assigned so as to indicate mutually the same landmarks between the landmarks detected from a scanogram image and the landmarks detected from the virtual patient image. However, possible embodiments are not limited to this example. It is possible to perform the matching process by using any arbitrary sets of landmarks.

For example, as illustrated in FIG. 8, when matching the landmarks identified with the identification codes "V1", "V2", and "V3" in the virtual patient image, with the landmarks identified with the identification codes "V1", "V2" and "V3" in the scanogram image, the position matching function 37b brings the coordinate spaces of the images in association with each other by performing a coordinate transformation process so as to minimize positional deviations between the pairs of mutually-the-same landmarks. For example, as illustrated in FIG. 8, the position matching function 37b calculates a coordinate transformation matrix "H" presented below, so as to minimize a sum "LS" of positional deviations between "V1 (x1,y1,z1) and C1 (X1, Y1,Z1)", between "V2 (x2,y2,z2) and C2(X2,Y2,Z2)", and between "V3 (x3,y3,z3) and C3 (X3,Y3,Z3)" that are pairs of anatomically the same landmarks.

$$LS=((X1,Y1,Z1)-H(x1,y1,z1))+((X2,Y2,Z2)-H(x2,y2,z2))+((X3,Y3,Z3)-H(x3,y3,z3))$$

Figure 9:
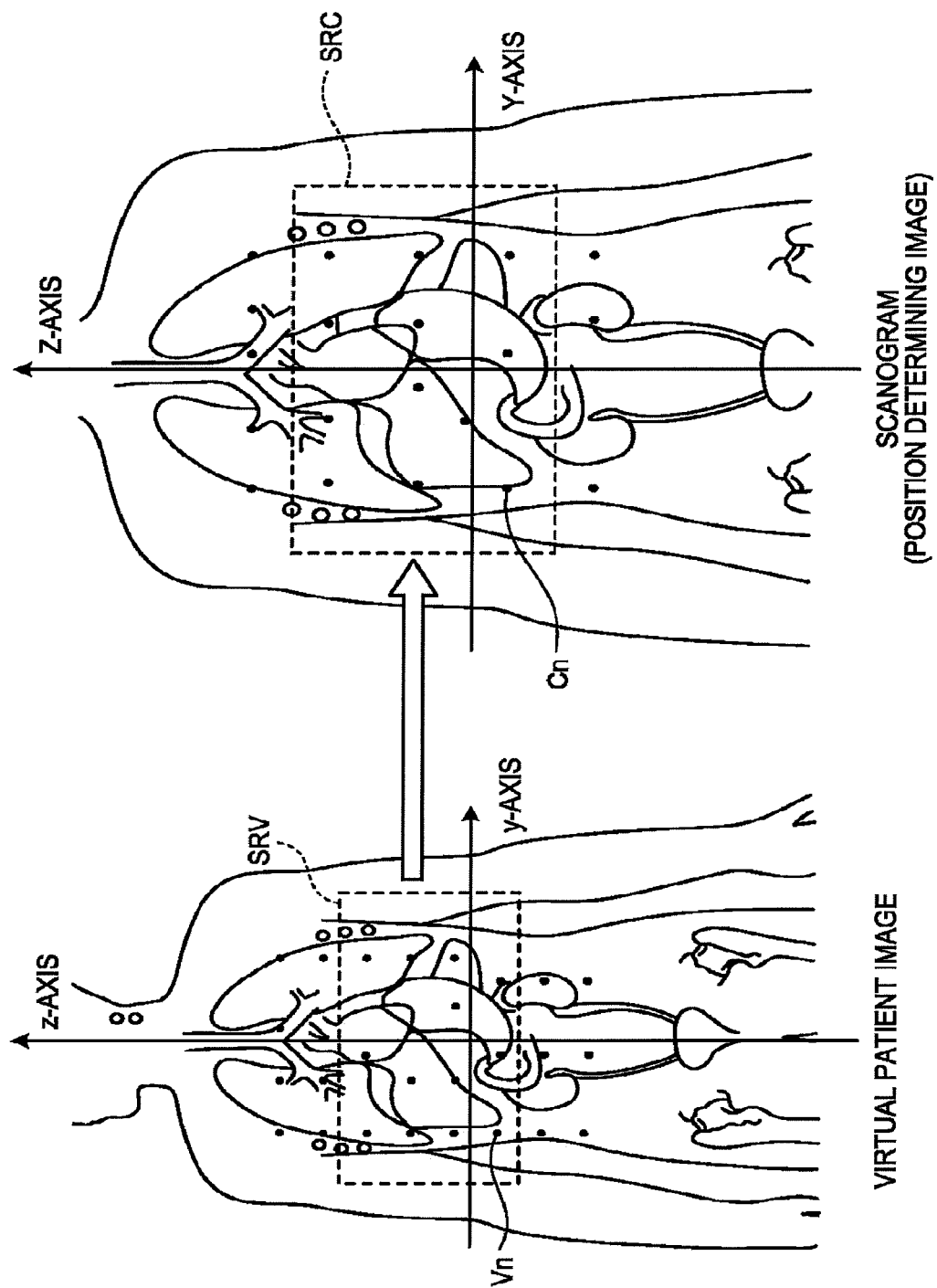
FIG. 9 is a drawing illustrating an example of a scan range transforming process performed by a coordinate transforming process according to the first embodiment.

By using the calculated coordinate transformation matrix "H", the position matching function 37b is able to transform the scan range designated in the virtual patient image into a scan range within the position determining image. For example, by using the coordinate transformation matrix "H", the position matching function 37b is able to transform a scan range "SRV" designated in the virtual patient image into a scan range "SRC" within the position determining image, as illustrated in FIG. 8. FIG. 9 is a drawing illustrating an example of the scan range transformation process using the coordinate transformation according to the first embodiment. For example, as illustrated in the virtual patient image in FIG. 9, when the operator sets the scan range "SRV" in the virtual patient image, the position matching function 37b transforms the set scan range "SRV" into the scan range "SRC" in the scanogram image, by using the coordinate transformation matrix explained above.

As a result, for example, the scan range "SRV" set in the virtual patient image so as to include the landmark corresponding to the identification code "Vn" is set into the scanogram image as being transformed into the scan range "SRC" including the identification code "Cn" corresponding to the same landmark. The coordinate transformation matrix "H" explained above may be stored in the storage circuitry 35 for each patient P so as to be read and used as necessary or may be calculated every time a scanogram image is acquired. As explained herein, according to the first embodiment, by having the virtual patient image displayed for the purpose of designating a range at the time of a pre-set operation and planning a position and a range within the virtual patient image, it is possible to automatically set the position and the range within the position determining image corresponding to the planned position and range by using numerical values, after taking the position determining image (the scanogram image).

Returning to the description of FIG. 2, on the basis of the information related to the positions of the landmarks, the appending function 37c is configured to determine position information of a scan range for the patient P expressed as an absolute position in an image taking system and to append the position information to an image. When there was at least one medical examination performed on the patient P in the past that includes the scan range of a scheduled scan, the controlling function 37d is configured to set a scan range of a main scan that is scheduled to be performed on the patient P, by referring to the position information appended to an image from the past (hereinafter, "past image") generated in the medical examination. The appending function 37c and the controlling function 37d will be explained in detail later.

An overall configuration of the medical information processing system 100 and the exemplary configuration of the X-ray CT apparatus 1 according to the first embodiment have thus been explained. The X-ray CT apparatus 1 according to the first embodiment configured as described above improves operability in the process of setting an image taking position or the like in advance, by executing the detecting function 37a and the position matching function 37b, for example.

Incidentally, when a medical examination is performed by the X-ray CT apparatus 1, the user may wish to perform a main scan under a scan condition that is the same as the scan condition used for an image generated in the past, for the purpose of making a comparison with the image generated in the past. In that situation, a conventional X-ray CT apparatus is configured to set a scan condition of the main scan in the current medical examination, by referring to a scan range of the main scan performed in the past medical examination. In this situation, the scan range is set as a relative position, and is not determined as an absolute position. More specifically, the conventional X-ray CT apparatus is configured to set a scan starting position according to a subjective judgment of the operator, every time a scan is performed. Further, the conventional X-ray CT apparatus is configured to set the scan range by using the scan starting position as a reference. For this reason, when medical examinations are performed by using the conventional X-ray CT apparatus, the scan starting position may vary among the medical examinations. Accordingly, when medical examinations are performed by using the conventional X-ray CT apparatus, there may be some situations where it is not be possible to accurately compare an image generated in the past with an image newly generated in a current medical examination, for the reason that, for example, the site to be compared is not properly rendered.

To cope with these situations, the X-ray CT apparatus 1 according to the first embodiment is configured to manage the scan range as an absolute position in the image taking system, on the basis of information related to positions of landmarks of the patient P. For example, the X-ray CT apparatus 1 according to the first embodiment performs a position information appending process of appending position information obtained by expressing the scan range as the absolute position in the image taking system to a generated image. Further, when there was at least one medical examination performed on the patient P in the past that includes the scan range of a scheduled scan, the X-ray CT apparatus 1 according to the first embodiment is configured to perform a scan range setting process of setting the scan range of the main scan in the current medical examination by referring to position information of the scan range used in the past medical examination. These functions are realized by the appending function 37c and the controlling function 37d. In the following sections, the appending function 37c and the controlling function 37d will be explained.

Figure 10:
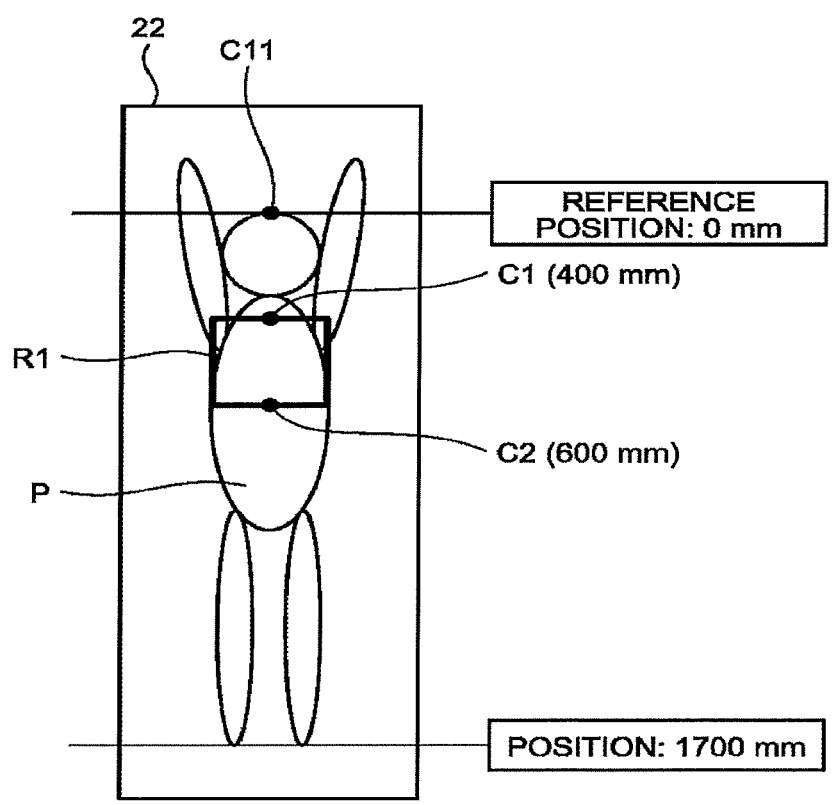
FIG. 10 is a first drawing for explaining the first embodiment.

The appending function 37c is configured to determine the position information within the image taking system with respect to landmarks and appends the position information to an image. In this situation, as the position information, the appending function 37c determines position information in the image taking system, with respect to the landmarks indicating the scan range of the patient P and further appends the position information to the image. FIG. 10 is a first drawing for explaining the first embodiment. FIG. 10 illustrates the patient P placed on the couchtop 22 of the couch 20. In this situation, it is assumed that a mark has been put on the couchtop 22 so that the patient P is placed on the couchtop 22 in such a manner that the vertex of the patient P is aligned with the mark. In other words, when the position information appending process is performed, the patient P is placed on the couchtop 22 in such a manner that the vertex of the patient P is aligned with the mark put on the couchtop 22. In the following sections, an example will be explained in which the vertex of the patient P is used as a reference position "0 mm" expressed as an absolute position in the image taking system. In other words, when the patient P is placed so that the vertex is aligned with the mark, the absolute position of the vertex of the patient P is expressed as "0 mm". In the following sections, the reference position expressed as an absolute position in the image taking system may simply be referred to as a "reference position". Further, such a position of the patient P aligned with the position of the mark put on the couchtop 22 will be referred to as a "couchtop reference position". In this situation, when the patient P is placed on the couchtop 22 so that the vertex of the patient P is aligned with the mark, while the vertex of the patient P is used as the reference position expressed as an absolute position in the image taking system, the "reference position" is the same as the "couchtop reference position". Further, as an alternative to the arrangement described above in which the patient P is placed on the couchtop 22 in such a manner that a predetermined site of the patient P is aligned with the mark put on the couchtop 22, another arrangement is also acceptable in which the patient P is placed on the couchtop 22 in such a manner that a predetermined site of the patient P is aligned with a location indicated by a light beam radiated onto the couchtop 22 from a light projector with which the gantry 10 is provided. This alternative arrangement is similarly applicable to any of the embodiments described below.

Further, when the height of the patient P is 170 cm, for example, the absolute position of the tip of the toes of the patient P is expressed as "1,700 mm" as illustrated in FIG. 10. In the present embodiment, an example will be explained in which the vertex of the patient P is used as the reference position "0 mm" expressed as an absolute position in the image taking system; however, any site other than the vertex of the patient P may be used as the reference position "0 mm" expressed as an absolute position in the image taking system. For example, while another site is used as a reference value, when the vertex is at "−500 mm", whereas the tip of the toes is at "1,200 mm", each being expressed with a relative value, the appending function 37c determines the tip of the toes to be at "1,700 mm", by determining the vertex to be at "0 mm".

The appending function 37c identifies absolute positions in the image taking system with respect to the positions set as the scan range of the main scan. In this situation, as the absolute positions in the image taking system, the appending function 37c uses a result of the AL analysis. As an example, a situation will be explained in which a region R1 illustrated in FIG. 10 is set as a scan range of the main scan. Further, it is assumed that, as a result of the AL analysis, a landmark C11 corresponding to the vertex, a landmark C1 positioned at the upper end of the region R1, and a landmark C2 positioned at the lower end of the region R1 have been identified. In that situation, the appending function 37c determines a range from the absolute position of the landmark C1 to the absolute position of the landmark C2 as the scan range of the main scan. More specifically, when the distance from the landmark C11 (the vertex) to the landmark C1 is assumed to be 400 mm, while the distance from the landmark C11 (the vertex) to the landmark C2 is assumed to be 600 mm, the appending function 37c determines, as the position information indicating the reference position and the scan range, "the reference position: the landmark C11 (the vertex); the landmark C1: 400 mm; and the landmark C2: 600 mm", for example. When the "reference position" is the same as the "couchtop reference position", the appending function 37c does not need to include the couchtop reference position in the position information.

Subsequently, the appending function 37c appends the determined position information to a CT image generated in the main scan. For example, the appending function 37c stores the determined position information into a DICOM tag attached to the generated CT image.

Figure 11:
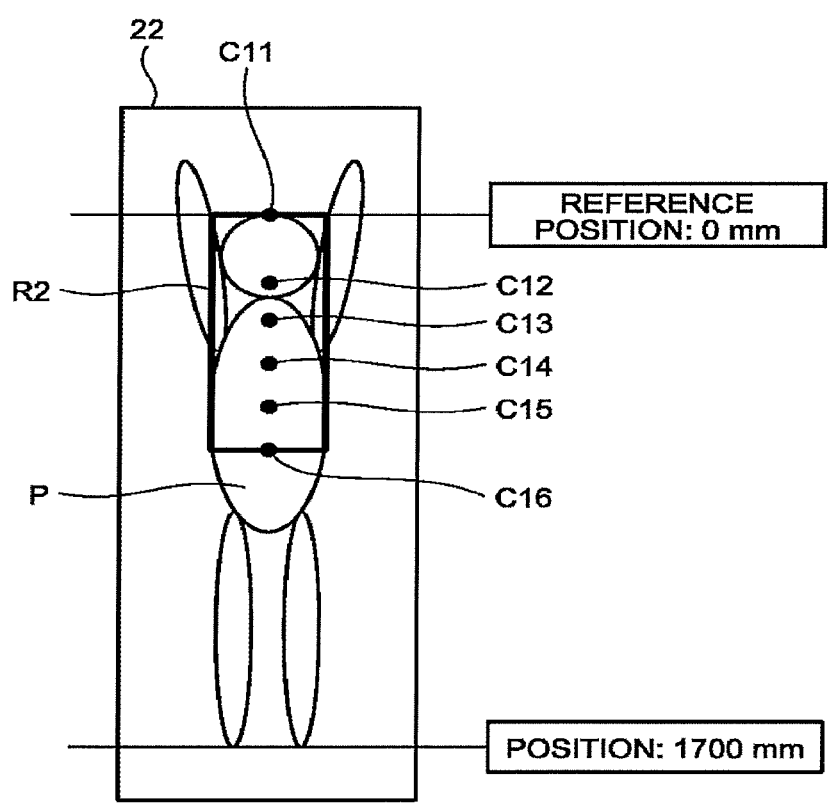
FIG. 11 is a second drawing for explaining the first embodiment.

Further, when a plurality of sites is to be scanned, the appending function 37c determines position information obtained by expressing the scan range of each of the scanned sites as an absolute position in the image taking system. For example, when having received a setting of a scan range spreading over a plurality of sites, the appending function 37c determines a piece of position information for each of the scanned sites and appends the determined pieces of position information corresponding to the various sites to a CT image. More specifically, when a scan is to be performed in a range spreading over the head, the neck, the chest, and the abdomen, the appending function 37c determines a piece of position information for each of the sites, namely, the head, the neck, the chest, and the abdomen. FIG. 11 is a second drawing for explaining the first embodiment. With reference to FIG. 11, an example will be explained in which a region R2 is set as a scan range of the main scan for the patient P illustrated in FIG. 10. It is assumed that the region R2 illustrated in FIG. 11 includes landmarks C11 to C16. For example, the appending function 37c determines that the position information of the head reads "the reference position: the landmark C11 (the vertex); the landmark C11: 0 mm; and the landmark C12: 200 mm". The appending function 37c determines that the position information of the neck reads "the reference position: the landmark C11 (the vertex); the landmark C12: 200 mm; and the landmark C13: 300 mm". The appending function 37c determines that the position information of the chest reads "the reference position: the landmark C11 (the vertex); the landmark C13: 300 mm; and the landmark C15: 650 mm". The appending function 37c determines that the position information of the abdomen reads "the reference position: the landmark C11 (the vertex); the landmark C14: 600 mm; and the landmark C16: 800 mm". As illustrated in FIG. 11, for example, in the range between the absolute position 600 mm and the absolute position 650 mm, the chest and the abdomen overlap with each other. When a plurality of organs is rendered in any single absolute position in this manner, the appending function 37c appends pieces of position information corresponding to the plurality of sites to a single CT image. With this arrangement, for example, when the CT image is divided into sections corresponding to a series, it is possible to separate the CT image into sections corresponding to the series for each of the sites, on the basis of the position information. As a result, it is possible to display the CT image separated into the sections in correspondence with the series.

Figures 12, 13:
FIG. 12 is a third drawing for explaining the first embodiment.
FIG. 13 is a fourth drawing for explaining the first embodiment.

When having received the protocol pre-set selecting operation via the input circuitry 31, the controlling function 37d judges whether or not there was a medical examination performed on the patient P in the past that includes the scan range of the scheduled scan. For example, the controlling function 37d searches in a medical examination history stored in the server apparatus 2, for example, for a piece of medical examination information that has the same patient identifier (ID) and the same scan range. In this situation, when having determined that there is at least one piece of medical examination information found in the search, the controlling function 37d sets a scan range of the main scan by referring to the position information appended to the DICOM tag of the past image generated in the past medical examination. For example, the controlling function 37d identifies the past image generated in the past medical examination on the basis of the piece of medical examination information and obtains the position information from the DICOM tag of the past image. Further, the controlling function 37d reads the reference position and the scan range that is included as the position information and sets the scan range of the current medical examination on the basis of the reference position and the scan range that were read. FIG. 12 is a third drawing for explaining the first embodiment. FIG. 12 illustrates an example in which the reference position read from the obtained position information is the landmark C11 (the vertex) at the absolute position 0 mm, whereas the scan range is a range from the landmark C1 (at the absolute position 400 mm) to the landmark C2 (at the absolute position 600 mm). Further, in the present example, it is assumed that, when the scan range setting process is performed, the patient P is placed in the same position on the couchtop 22 as when the position information appending process is performed. In other words, when the scan range setting process is performed, the patient P is placed on the couchtop 22 in such a manner that the vertex of the patient P is aligned with the mark put on the couchtop 22. In that situation, the controlling function 37d sets the scan range to be used during the main scan, by using the obtained position information. For example, as the scan range to be used during the main scan, the controlling function 37d sets a scan range from the landmark C1 at the absolute position 400 mm in the image taking system to the landmark C2 at the absolute position 600 mm in the image taking system, while using the landmark C11 (the vertex) as the reference position. Because the X-ray CT apparatus 1 is configured to set the scan range of the main scan in this manner, with reference to the position information appended to the past image, the X-ray CT apparatus 1 is able to omit the position determining scan. As a result, it is possible to reduce the radiation exposure amount of the patient P.

Further, for example, when there is a plurality of pieces of medical examination information found in the search, the controlling function 37d sets a scan range of the main scan, by referring to the position information appended to the most recent past image among the past images. FIG. 13 is a fourth drawing for explaining the first embodiment. The upper section of FIG. 13 illustrates the position information appended to a CT image generated in the second to the last medical examination. The lower section of FIG. 13 illustrates the position information appended to a CT image generated in the last (the most recent) medical examination. In the example illustrated in FIG. 13, the positions of the landmarks C1 and C2 in the last medical examination are farther from the reference position than those positions were in the second to the last medical examination. In that situation, the controlling function 37d sets the scan range of the main scan by referring to the position information appended to the CT image generated in the last medical examination, and not the position information appended to the CT image generated in the second to the last medical examination.

Figure 14:
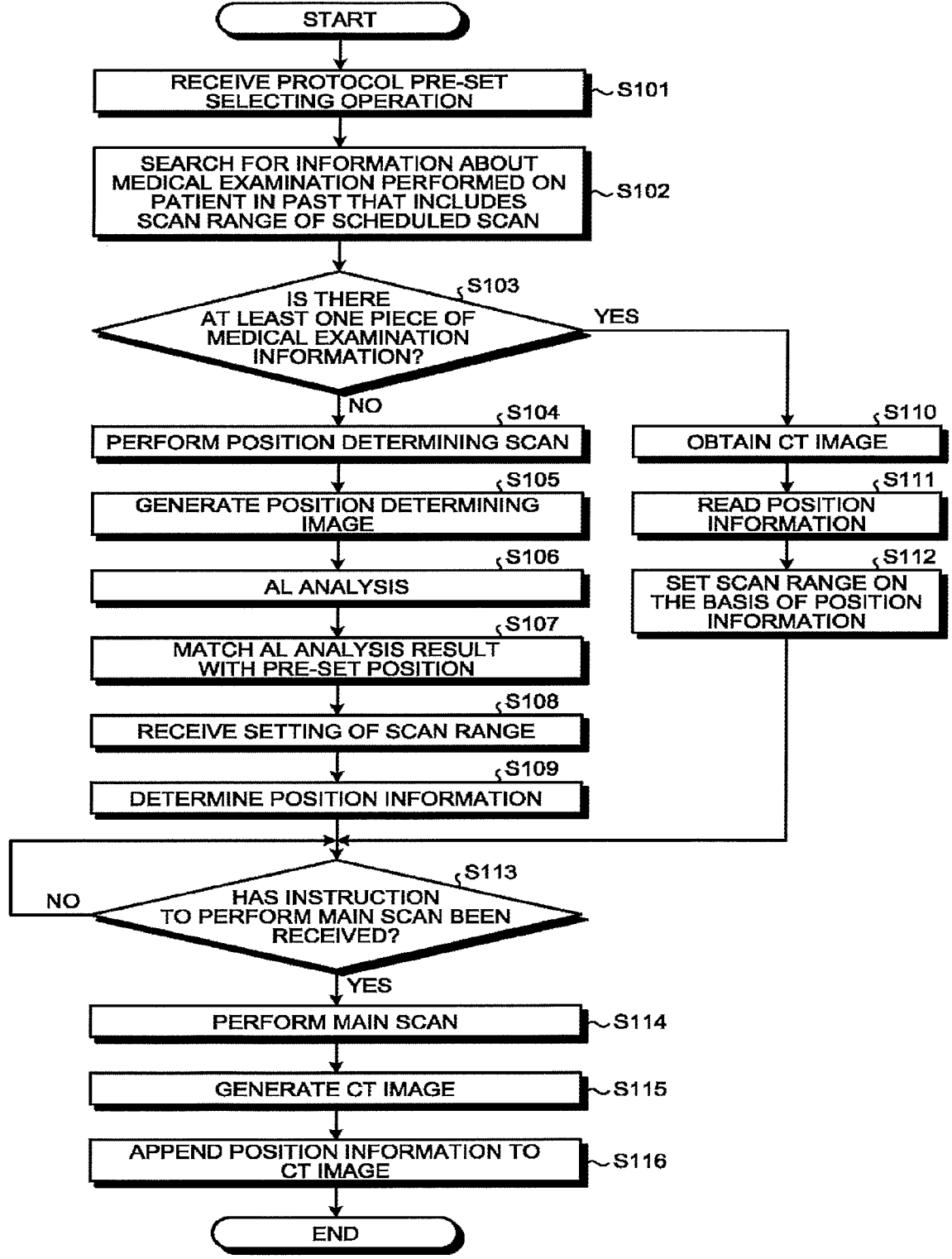
FIG. 14 is a flowchart illustrating a processing procedure performed by an X-ray CT apparatus according to the first embodiment.

FIG. 14 is a flowchart illustrating a processing procedure performed by the X-ray CT apparatus 1 according to the first embodiment. FIG. 14 illustrates the flowchart for explaining operations of the entire X-ray CT apparatus 1, while explaining which step in the flowchart corresponds to each of the constituent elements.

Step S101 is a step realized by the input circuitry 31. At step S101, the input circuitry 31 receives a protocol pre-set selecting operation. Steps S102 and S103 are steps corresponding to the controlling function 37d. At these steps, as a result of the processing circuitry 37 invoking and executing a predetermined program corresponding to the controlling function 37d from the storage circuitry 35, the controlling function 37d is realized. At step S102, the controlling function 37d searches in the medical examination history stored in the server apparatus 2, for example, a piece of medical examination information performed on the patient P in the past that includes the scan range of the scheduled scan, on the basis of the protocol pre-set operation received at step S101.

At step S103, the controlling function 37d judges whether or not there is at least one piece of medical examination found in the search at step S102. When the controlling function 37d determines that there is at least one piece of medical examination (step S103: Yes), the process proceeds to step S110 where the X-ray CT apparatus 1 performs the scan range setting process. On the contrary, when the controlling function 37d determines that there is no piece of medical examination information (step S103: No), the process proceeds to step S104 where the X-ray CT apparatus 1 performs the position information appending process. There may be some situations where an existing piece of medical examination corresponds to an exhalation period while the scheduled image taking process is to be performed during an inhalation period or where the patient needs to undergo surgery even where there is a piece of medical examination information. In those situations, it is desirable to have the X-ray CT apparatus 1 perform the position information appending process. For this reason, the operator may forcibly cause the process to proceed to step S104 even when there are one or more pieces of medical examination information. For example, even when the controlling function 37d determines at step S103 that there is at least one piece of medical examination, the process proceeds to step S104 when an instruction is received from the operator.

Step S104 is a step realized by the scan controlling circuitry 33. At step S104, the scan controlling circuitry 33 performs a position determining scan. Step S105 is a step realized by the image reconstructing circuitry 36. At step S105, the image reconstructing circuitry 36 generates a position determining image.

Step S106 is a step corresponding to the detecting function 37a. At this step, as a result of the processing circuitry 37 invoking and executing a predetermined program corresponding to the detecting function 37a from the storage circuitry 35, the detecting function 37a is realized. At step S106, the detecting function 37a performs an AL analysis on the position determining image.

Step S107 is a step corresponding to the position matching function 37b. At this step, as a result of the processing circuitry 37 invoking and executing a predetermined program corresponding to the position matching function 37b from the storage circuitry 35, the position matching function 37b is realized. At step S107, the position matching function 37b matches the result of the AL analysis with the pre-set position.

Figure 15:
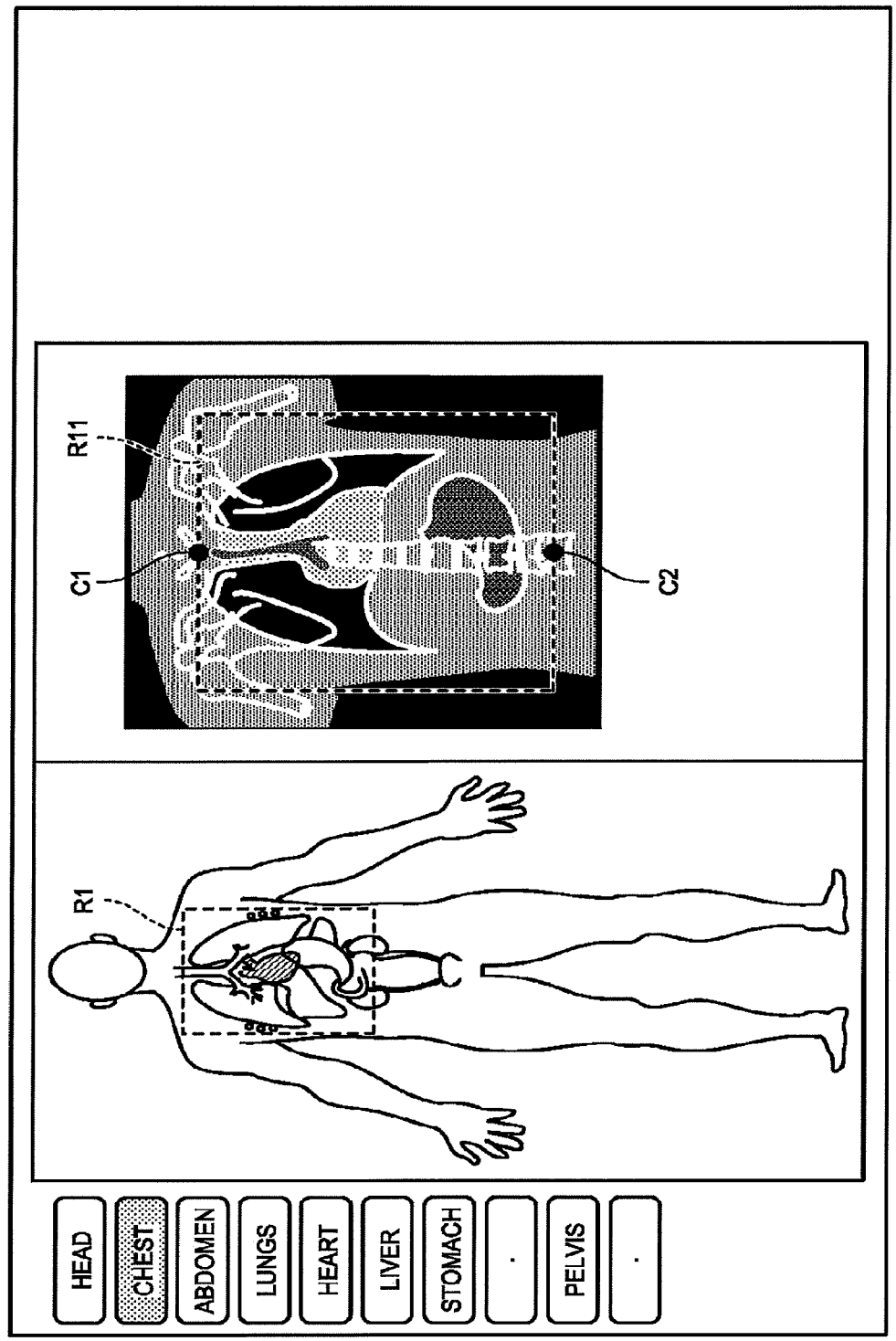
FIG. 15 is a fifth drawing for explaining the first embodiment.

Step S108 is a step realized by the input circuitry 31. At step S108, the input circuitry 31 receives the setting of the scan range. FIG. 15 is a fifth drawing for explaining the first embodiment. FIG. 15 illustrates a GUI screen corresponding to a situation where a position determining image has been taken after the chest is set as a target site in the pre-set operation of the main scan. As illustrated in FIG. 15, the GUI screen displays, on the left side thereof, buttons (e.g., buttons representing the head, the chest, the abdomen, the lungs, the heart, and/or the like) used for designating a target site, as well as a virtual patient image rendering an entire human body, and the position determining image obtained by performing the position determining scan. Further, FIG. 15 illustrates a situation where the scan range R1 corresponding to the chest is set in the virtual patient image. As a result of the scan range R1 being set in the virtual patient image, the position matching function 37b transforms the scan range R1 into coordinate information expressed in the position determining image so as to set a scan range R11. In this situation, it is possible to change, as appropriate, the scan range R1 set in the virtual patient image, when an operation to enlarge or reduce the scan range R1 is received from the operator on the GUI screen.

Returning to the description of FIG. 14, step S109 is a step corresponding to the appending function 37c. At this step, as a result of the processing circuitry 37 invoking and executing a predetermined program corresponding to the appending function 37c from the storage circuitry 35, the appending function 37c is realized. At step S109, the appending function 37c generates position information. For example, the appending function 37c determines position information obtained by expressing the scan range for the patient P as an absolute position in the image taking system, on the basis of the information related to the positions of the landmarks. In this situation, for example, when the reference position is the vertex, the appending function 37c determines that the position information of the scan range R11 illustrated in FIG. 15 is defined by a range from the landmark C1 to the landmark C2. In this situation, the appending function 37c may determine position information with which positions in the virtual patient image based on an anatomical model of a human body are further kept in correspondence. In that situation, the appending function 37c may determine position information on the basis of the position of the landmark at the upper end of the scan range R1 and the position of the landmark at the lower end of the scan range R1 within the virtual patient image. After the process at step S109 is finished, the X-ray CT apparatus 1 according to the first embodiment proceeds to step S113.

Steps S110 to S112 are steps corresponding to the controlling function 37d. At these steps, as a result of the processing circuitry 37 invoking and executing a predetermined program corresponding to the controlling function 37d from the storage circuitry 35, the controlling function 37d is realized. At step S110, the controlling function 37d obtains a CT image (a past image) stored in the server apparatus 2, for example. Subsequently, at step S111, the controlling function 37d reads the position information from information attached to the obtained CT image.

After that, at step S112, the controlling function 37d sets a scan range on the basis of the read position information. When the step S112 is finished, the X-ray CT apparatus 1 according to the first embodiment proceeds to step S113. Alternatively, the controlling function 37d may set a scan range or a scan condition by selecting a past image. For example, the controlling function 37d may set as many images as selected from within a past image as scan ranges. Further, as scan conditions, the controlling function 37d may set a Field OF View (FOV), an X-ray tube current, and an X-ray tube voltage of a past image.

Step S113 is a step realized by the scan controlling circuitry 33. At step S113, the scan controlling circuitry 33 judges whether or not an instruction to perform a main scan has been received. When it is determined that an instruction to perform the main scan has not been received (step S113: No), the scan controlling circuitry 33 repeatedly performs the judging process at step S113. On the contrary, when it is determined that an instruction to perform the main scan has been received (step S113: Yes), the scan controlling circuitry 33 performs the main scan at step S114. The scan controlling circuitry 33 performs the main scan on the scan range that was set. In this situation, the scan controlling circuitry 33 may determine the actual scan range by stretching the set scan range in the head-and-toe direction, for the purpose of ensuring that the set scan range will be imaged with certainty.

Step S115 is a step realized by the image reconstructing circuitry 36. At step S115, the image reconstructing circuitry 36 generates a CT image. Subsequently, step S116 is a step corresponding to the appending function 37c. At this step, as a result of the processing circuitry 37 invoking and executing a predetermined program corresponding to the appending function 37c from the storage circuitry 35, the appending function 37c is realized. At step S116, the appending function 37c appends the position information to the CT image.

As explained above, in the first embodiment, the position information is determined by expressing the scan range for the patient P as the absolute position in the image taking system on the basis of the information related to the positions of the landmarks, and the position information is appended to the image. In other words, the X-ray CT apparatus 1 according to the first embodiment is able to manage the scan range as the absolute position in the image taking system. Further, when there was at least one medical examination performed on the patient P in the past that includes the scan range of the scheduled scan, the X-ray CT apparatus 1 according to the first embodiment is configured to perform the scan range setting process of setting the scan range of the main scan in the current medical examination, by referring to the position information of the scan range used in the past medical examination. With these arrangements, because the X-ray CT apparatus 1 according to the first embodiment sets the scan range of the main scan by referring to the position information appended to the past image, the X-ray CT apparatus 1 is able to omit the position determining scan.

Figure 16:
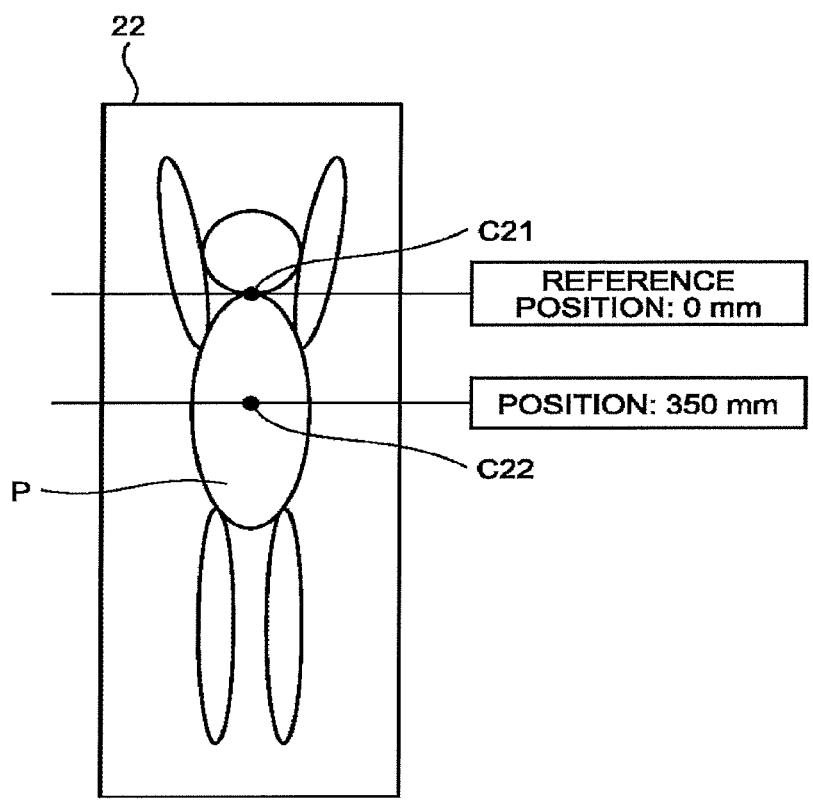
FIG. 16 is a sixth drawing for explaining the first embodiment.

In the first embodiment above, the example is explained in which the vertex of the patient P is used as the reference position "0 mm" expressed as the absolute position in the image taking system; however, possible embodiments are not limited to this example. For instance, a location other than the vertex of the patient P may be used as the reference position expressed as an absolute position in the image taking system. FIG. 16 is a sixth drawing for explaining the first embodiment. FIG. 16 illustrates an example in which a landmark C21 represented by the seventh cervical vertebra of the patient P is used as the reference position "0 mm" expressed as an absolute position in the image taking system. In this situation also, it is assumed that a mark has been put on the couchtop 22 so that the patient P is placed on the couchtop 22 in such a manner that the vertex is aligned with the mark. Further, the scan range is the range from the landmark C21 to the landmark C22 both of which were identified as a result of an AL analysis. In that situation, the appending function 37c determines the range from the absolute position of the landmark C21 to the absolute position of the landmark C22 as the scan range of the main scan. More specifically, when the distance from the landmark C21 (the seventh cervical vertebra) to the landmark C22 is assumed to be 350 mm, for example, the appending function 37c determines, as position information indicating the reference position and the scan range, "the reference position: the landmark C21 (the seventh cervical vertebra); the landmark C21: 0 mm; and the landmark C22: 350 mm". In this situation, when the reference position and the couchtop reference position expressed as absolute positions in the image taking system are different from each other, the appending function 37c further determines the couchtop reference position as another piece of position information. More specifically, as position information indicating that the patient P is placed on the couchtop 22 in such a manner that the vertex is aligned with the mark put on the couchtop 22, the appending function 37c determines "the couchtop reference position: the landmark C11: −350 mm". Subsequently, the appending function 37c appends the determined position information to a CT image generated by the main scan. For example, the appending function 37c stores the determined position "the reference position: the landmark C21 (the seventh cervical vertebra); the landmark C21: 0 mm; and the landmark C22: 350 mm; and the couchtop reference position: the landmark C11: −350 mm" into a DICOM tag attached to the generated CT image.

Further, when there is at least one piece of medical examination information found in the search at step S102, the controlling function 37d may, at step S114, cause the scan controlling circuitry 33 to acquire data under a scan condition that is the same as the scan condition used for the past image and may, at step S115, cause the image reconstructing circuitry 36 to reconstruct the image under a reconstruction condition that is the same as the reconstruction condition used for the past image. With these arrangements, for example, the medical doctor interpreting images is able to more accurately compare the past image with the image generated in the current medical examination.

Further, in the embodiment described above, the example is explained in which the landmarks are detected by performing the AL analysis on the position determining image, so that the position information is determined with respect to the detected landmarks; however, possible embodiments are not limited to this example. For instance, landmarks may be detected by performing an AL analysis on an image obtained from the main scan so that position information is determined with respect to the detected landmarks and is appended to the image. There may be some situations where, as described herein, the landmarks that are not accurately rendered in a position determining image obtained with a small radiation dose can be rendered as a result of the AL analysis performed after the main scan. In other words, performing the AL analysis after the main scan makes it possible to determine position information for each of the organs with a higher level of precision. Further, when a contrast-enhanced image taking process is performed, performing an AL analysis on an image after the contrast enhancement makes it possible to determine position information of structures such as blood vessels that were not rendered before the contrast enhancement. In that situation also, for example, the position information determined on the basis of the image after the contrast enhancement may further be appended to the position information appended to the image before the contrast enhancement.

Second Embodiment

In the first embodiment above, the example is explained in which the mark is put on the couchtop 22, so that when the position information appending process is performed and when the scan range setting process is performed, the patient P is placed on the couchtop 22 in such a manner that the vertex is aligned with the mark on the couchtop 22. In other words, the medical facility has the rule indicating that, when the position information appending process is performed and when the scan range setting process is performed, the patient P should be placed on the couchtop 22 in such a manner that the vertex is aligned with the mark on the couchtop 22. In that situation, as long as the position information has been obtained, it is possible to set a scan range without taking the couchtop reference position into consideration.

However, there may be some other situations where the facility has no such rule or where the position information appending process and the scan range setting process are performed separately in two facilities having mutually-different rules. In those situations, the position in which the patient P is placed on the couchtop 22 may be different between when the position information appending process is performed and when the scan range setting process is performed. For example, the patient P is placed in such a manner that the vertex of the patient P is aligned with the couchtop reference position when the position information appending process is performed, whereas the patient P is placed in such a manner that the tip of the toes of the patient P is aligned with the couchtop reference position when the scan range setting process is performed.

In that situation, it is necessary to set a scan range while taking the couchtop reference position into consideration. Thus, in a second embodiment, an example will be explained in which a scan range is set while taking the couchtop reference position into consideration. The configuration of an X-ray CT apparatus according to the second embodiment is the same as the configuration of the X-ray CT apparatus 1 according to the first embodiment, except that a part of the functions of the controlling function 37d is different. Accordingly, explanations of the constituent elements other than the controlling function 37d will be omitted.

Figure 17:
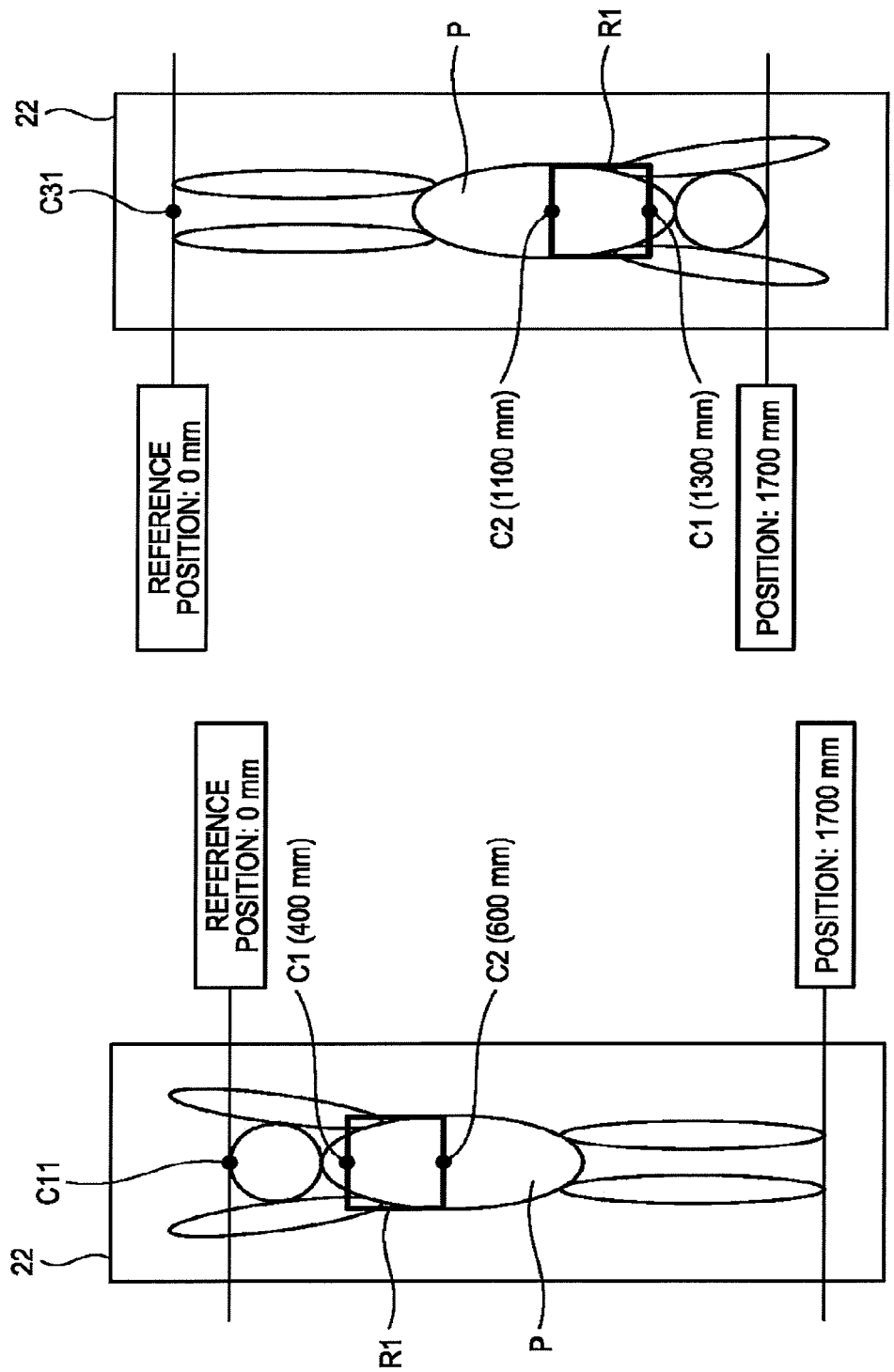
FIG. 17 is a drawing for explaining a second embodiment.

FIG. 17 is a drawing for explaining the second embodiment. FIG. 17 illustrates an example in which the patient P is placed on the couchtop 22 in such a manner that the vertex is aligned with the mark on the couchtop 22 when the position information appending process is performed, whereas the patient P is placed on the couchtop 22 in such a manner that the tip of the toes is aligned with the mark on the couchtop 22 when the scan range setting process is performed. The left section of FIG. 17 illustrates an example of the position information appending process being performed, whereas the right section of FIG. 17 illustrates an example of the scan range setting process being performed.

The left section of FIG. 17 illustrates a situation where, as a result of the position information appending process performed on a past image, position information is determined as "the reference position: the landmark C11 (the vertex); the landmark C1: 400 mm; the landmark C2: 600 mm; and the couchtop reference position: the landmark C11 (the vertex): 0 mm". Further, as illustrated in the right section of FIG. 17, when the scan range setting process is performed, the controlling function 37d obtains the reference position in the image taking system used during the main scan. For example, by receiving an input from the operator, the controlling function 37d obtains "the landmark C31 (the tip of the toes)" as the reference position used during the main scan and obtains "the landmark C31 (the tip of the toes): 0 mm" as the couchtop reference position used during the main scan.

After that, on the basis of the reference position in the image taking system used during the scan of the past image and the reference position in the image taking system used during the main scan each included in the position information, the controlling function 37d sets a scan range to be used during the main scan. For example, the controlling function 37d obtains information indicating that the height of the patient P is 1,700 mm, from medical examination information. Alternatively, the height of the patient P may be appended to the past image as position information. Further, the controlling function 37d transforms the position information determined by the position information appending process on the basis of the reference position of the main scan. For example, the controlling function 37d identifies the positions of the landmark C1 and the landmark C2, on the basis of the reference position in the past image, the reference position during the main scan, and the height and further transforms the position information determined by the position information appending process, into position information used during the main scan. More specifically, as the position information during the main scan, the controlling function 37d sets a scan range as "the reference position: the landmark C31 (the tip of the toes); the landmark C2: 1,100 mm; the landmark C1: 1,300 mm; and the couchtop reference position: the landmark C31 (the tip of the toes): 0 mm".

As explained above, in the second embodiment, it is possible to set the scan range of the main scan, even when the reference position in the past image is different from the reference position of the main scan. As a result, according to the second embodiment, because it is possible to omit the position determining scan, it is possible to reduce the radiation exposure amount of the patient P.

In the embodiment above, the example is explained in which the patient P is placed on the couchtop 22 in such a manner that the vertex is aligned with the mark on the couchtop 22 when the position information appending process is performed, whereas the patient P is placed on the couchtop 22 in such a manner that the tip of the toes is aligned with the mark on the couchtop 22 when the main scan is performed; however, possible embodiments are not limited to this example. For instance, the second embodiment is also applicable to the situation where, for example, the patient P is placed on the couchtop 22 in such a manner that the vertex is aligned with the mark on the couchtop 22 when the position information appending process is performed, whereas the patient P is placed on the couchtop 22 in such a manner that a shoulder of the patient P is aligned with the mark on the couchtop 22 when the main scan is performed. Further, in that situation, when the shoulder of the patient P is rendered in a past image, the controlling function 37d may set a scan range after performing an AL analysis on the past image and obtaining position information of the shoulder.

Further, when the patient P is placed on the couchtop 22 in such a manner that the shoulder is aligned with the mark on the couchtop 22 during the main scan, even when the shoulder of the patient P is not rendered in any past image, a scan range may be set by obtaining the height of the patient P and further estimating the distance from the vertex to the shoulder on the basis of the height. As for the distance from the vertex to the shoulder, various distances corresponding to different heights may be determined in advance according to a predetermined ratio. Alternatively, the distance from the vertex to the shoulder of the patient P may be calculated by comparing the information about the height of the patient P with the virtual patient data described above.

In the present embodiment, the example is explained in which the patient P is placed on the couchtop 22 in such a manner that the same site is aligned with the mark on the couchtop 22 both when the position information appending process is performed and when the scan range setting process is performed. However, when the image taking directions are different between the two processes, such as a "head-first" method by which the image taking process is started with the head and a "foot-first" method by which the image taking process is started with the tip of the toes, it is necessary to determine the position information used during the main scan, while taking the difference in the image taking direction in consideration. For example, when the image taking process is performed by using the "head-first" method when performing the position information appending process on the past image, the position information is determined as "the reference position: the landmark C11 (the vertex); the landmark C1: 400 mm; the landmark C2: 600 mm; and the couchtop reference position: the landmark C11

(the vertex): 0 mm". In contrast, when the main scan is performed by using the "foot-first" method, the position information used during the main scan is determined as "the reference position: the landmark C11 (the vertex); the landmark C1: −400 mm; the landmark C2: −600 mm; and the couchtop reference position: the landmark C11 (the vertex): 0 mm".

A Modification Example of Second Embodiment

Figure 18:
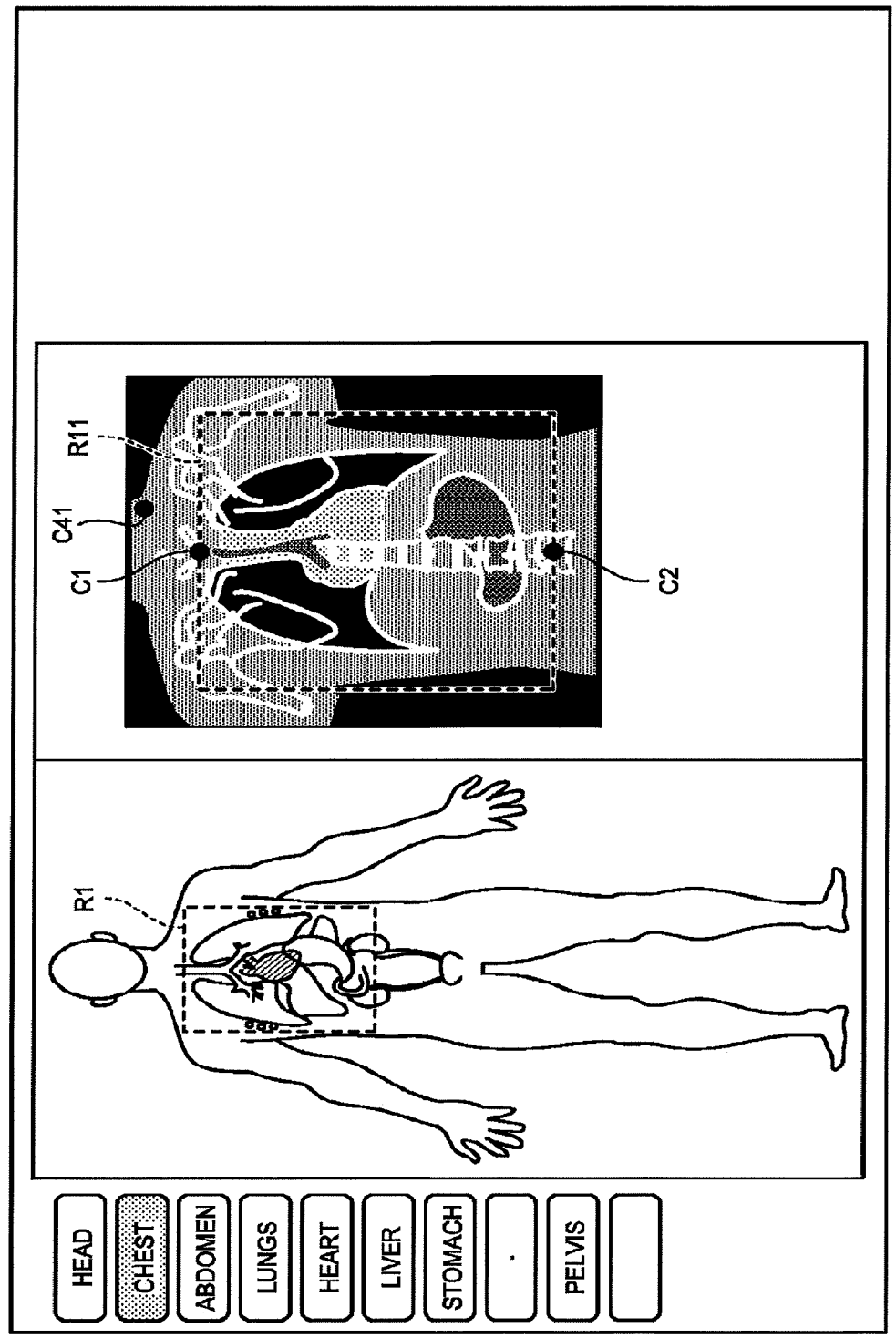
FIG. 18 is a drawing for explaining a modification example of the second embodiment.

In the second embodiment above, the example is explained in which the reference position in the image taking system used during the main scan is obtained; however, possible embodiments are not limited to this example. For instance, a reference position may be determined in accordance with a scanned site. FIG. 18 is a drawing for explaining a modification example of the second embodiment.

FIG. 18 illustrates a GUI screen in an example where the chest is set as a target site during a protocol pre-set operation of a main scan. As illustrated in FIG. 18, the GUI screen displays, on the left side thereof, buttons (e.g., buttons representing the head, the chest, the abdomen, the lungs, the heart, and/or the like) used for designating a target site, as well as a virtual patient image rendering an entire human body, and a past image. FIG. 18 illustrates the past image in which the scan range of the main scan is indicated as R11, while the region corresponding to R11 in the virtual patient image is indicated as R1.

Further, in accordance with the scanned site, the controlling function 37d identifies the reference position in the image taking system used during the main scan on the basis of a plurality of landmarks in the past image. In this situation, in the present modification example of the second embodiment, it is assumed that, in accordance with the scanned site, the storage circuitry 35 stores therein a table in which candidates for the reference position to be used during the main scan are set in advance. When the chest is selected in the protocol pre-set operation, the controlling function 37d reads the table from the storage circuitry 35 and selects, for example, a landmark indicated as C41 in the past image in FIG. 18, as the reference position to be used during the main scan.

After that, the controlling function 37d sets a scan range to be used during the main scan, on the basis of the identified reference position in the image taking system to be used during the main scan and the position information in the past image. For example, as the position information used during the main scan, the controlling function 37d sets a scan range as "the reference position: the landmark C41 (the shoulder); the landmark C1: 50 mm; the landmark C1: 250 mm; and the couchtop reference position: the landmark C41 (the tip of the toes): 0 mm".

Subsequently, the controlling function 37d instructs that the reference position be aligned with the mark on the couchtop 22. For example, when the shoulder is identified as the reference position, the controlling function 37d causes the display 32 to display an instruction indicating that the shoulder of the patient P should be aligned with the mark on the couchtop 22. Alternatively, the controlling function 37d may output an audible instruction or an alarm sound to indicate that the reference position be aligned with the mark on the couchtop 22.

As explained above, in the modification example of the second embodiment, even when the reference position in the past image and the reference position of the main scan are not defined in rules, it is possible to set the scan range of the main scan, by determining the reference position of the main scan from the past image. As a result, according to the second embodiment, because it is possible to omit the position determining scan, it is possible to reduce the radiation exposure amount of the patient P.

Further, when a plurality of candidates for the reference position is detected, the controlling function 37d may be configured to receive a selection of the reference position from the operator. Alternatively, when a plurality of candidates for the reference position is detected, the controlling function 37d may be configured to set a reference position while taking the image taking direction into consideration. For example, as the image taking direction designated during the protocol pre-set operation, the controlling function 37d judges which method has been selected from between the "head-first" method by which the image taking process is started from the head and the "foot-first" method by which the image taking process is started from the tip of the toes. Further, the controlling function 37d identifies a reference position that is positioned to be imaged before the scan range is, from among the plurality of candidates for the reference position corresponding to the scanned site. For example, let us discuss an example in which, when the scanned site is the chest, a shoulder and the celiac plexus are detected as candidates for the reference position. In that situation, the controlling function 37d identifies the shoulder as the reference position used during the main scan when the "head-first" method is selected and identifies the celiac plexus as the reference position used during the main scan when the "foot-first" method is selected. As another example, when the reference positions are not included in the scan range, the controlling function 37d may be configured to identify one of the reference positions located closer to the one of the two ends of the scan range to be imaged first (i.e., the scan starting position). For example, let us discuss an example in which the scanned site is the chest, and the vertex and the tip of the toes are detected as candidates for the reference position. In that situation, the controlling function 37d identifies the vertex as the reference position used during the main scan when the "head-first" method is selected and identifies the tip of the toes as the reference position used during the main scan when the "foot-first" method is selected. Alternatively, as explained above, one reference position may be identified from among a plurality of candidates for the reference position, on the basis of the distances from the scan starting position. In another example, one reference position may be identified from among a plurality of candidates for the reference position, on the basis of the distances from an intermediate position including the center of the scan range.

Third Embodiment

In the embodiments above, the example is explained in which the process of determining the scan range to be used during the main scan is performed while the landmarks of the patient P are kept in correspondence with the position information of the landmarks in the image taking system used during the scan of the past image.

In this regard, there may be some situations where an image of the same patient from the past may be available in which the same scan range was imaged but to which no position information is appended. In those situations, it is also acceptable to set a scan range by obtaining, when the main scan is started, position information by performing an AL analysis on the past image and using the obtained position information.

Accordingly, as a third embodiment, an example will be explained in which the scan range setting process is performed by using an image to which no position information is appended. The configuration of an X-ray CT apparatus according to the third embodiment is the same as the configuration of the X-ray CT apparatus 1 according to the first embodiment, except that a part of the functions of the controlling function 37d is different. For this reason, explanations of the constituent elements other than the controlling function 37d will be omitted.

Figure 19:
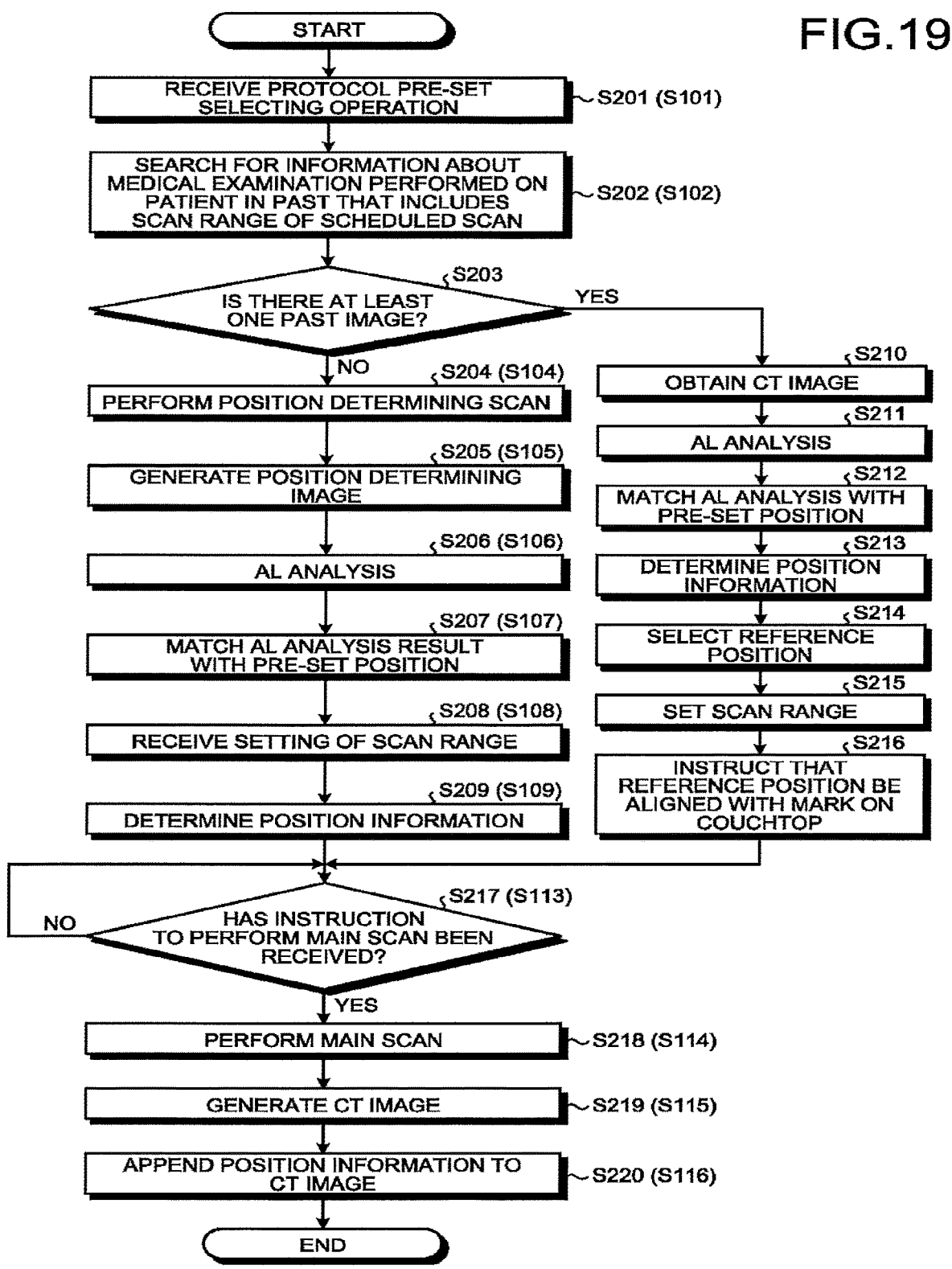
FIG. 19 is a flowchart illustrating a processing procedure performed by an X-ray CT apparatus according to a third embodiment.

FIG. 19 is a flowchart illustrating a processing procedure performed by the X-ray CT apparatus according to the third embodiment. FIG. 19 illustrates a flowchart for explaining operations of the entire X-ray CT apparatus 1, while explaining which step in the flowchart corresponds to each of the constituent elements. The processes at steps S201 and S202 in FIG. 19 correspond to the processes at steps S101 and S102 in FIG. 14. Further, the processes at steps S204 through S209 in FIG. 19 correspond to the processes at steps S104 through S109 in FIG. 14.

Step S203 is a step corresponding to the controlling function 37d. At this step, as a result of the processing circuitry 37 invoking and executing a predetermined program corresponding to the controlling function 37d from the storage circuitry 35, the controlling function 37d is realized. At step S203, the controlling function 37d judges whether or not there is at least one past image corresponding to the medical examination information found in the search at step S202. In this situation, when the controlling function 37d determines that there is at least one past image corresponding to the medical examination information (step S203: Yes), the process proceeds to step S210. On the contrary, when the controlling function 37d determines that there is no past image corresponding to the medical examination information (step S203: No), the process proceeds to step S204.

Steps S210 and S211 are steps corresponding to the controlling function 37d. At these steps, as a result of the processing circuitry 37 invoking and executing a predetermined program corresponding to the controlling function 37d from the storage circuitry 35, the controlling function 37d is realized. At step S210, the controlling function 37d obtains a CT image (a past image) stored in the server apparatus 2, for example. Step S211 is a step corresponding to the detecting function 37a. At this step, as a result of the processing circuitry 37 invoking and executing a predetermined program corresponding to the detecting function 37a from the storage circuitry 35, the detecting function 37a is realized. At step S211, the detecting function 37a performs an AL analysis on the past image.

Step S212 is a step corresponding to the position matching function 37b. At this step, as a result of the processing circuitry 37 invoking and executing a predetermined program corresponding to the position matching function 37b from the storage circuitry 35, the position matching function 37b is realized. At step S212, the position matching function 37b matches the result of the AL analysis with the pre-set position.

Step S213 is a step corresponding to the appending function 37c. At this step, as a result of the processing circuitry 37 invoking and executing a predetermined program corresponding to the appending function 37c from the storage circuitry 35, the appending function 37c is realized. At step S213, the appending function 37c generates position information. For example, with respect to the positions of the landmarks, the appending function 37c determines position information in the image taking system used during the scan of the past image.

Steps S214 through S216 are steps corresponding to the controlling function 37d. At these steps, as a result of the processing circuitry 37 invoking and executing a predetermined program corresponding to the controlling function 37d from the storage circuitry 35, the controlling function 37d is realized. At step S214, the controlling function 37d selects a reference position. For example, the controlling function 37d identifies the reference position in the image taking system during the main scan, on the basis of the plurality of landmarks in the past image, in accordance with the scanned site.

At step S215, the controlling function 37d sets a scan range. For example, by using the method explained in the modification example of the second embodiment, the controlling function 37d sets a scan range used during the main scan, on the basis of the identified reference position in the image taking system used during the main scan and the position information.

At step S216, the controlling function 37d instructs that the reference position be aligned with the mark on the couchtop 22. For example, when a shoulder is identified as the reference position, the controlling function 37d causes the display 32 to display an instruction indicating that the shoulder of the patient P be aligned with the mark on the couchtop 22. When step S216 is finished, the process proceeds to step S217. The processes at steps S217 through S220 in FIG. 19 correspond to the processes at steps S113 through S116 in FIG. 14.

As explained above, in the third embodiment, even when no position information is appended to the past image, it is possible to set the scan range of the main scan by using the past image. As a result, according to the third embodiment, because it is possible to omit the position determining scan, it is possible to reduce the radiation exposure amount of the patient P.

In the third embodiment, the example is explained in which, when the main scan is started, the AL analysis is performed on the past image to which no position information is appended; however, possible embodiments are not limited to this example. For instance, the controlling function 37d may, when the main scan is started, perform the AL analysis on a past image to which a reference position is appended as position information. In another example, the controlling function 37d may, when the main scan is started, perform the AL analysis on a past image to which a reference position and a scan range are appended as position information. In that situation, when setting a scan range, the controlling function 37d may set the scan range by using the reference position appended to the past image.

Fourth Embodiment

In the first to the third embodiments, the example is explained in which the position information generated in the past medical examination performed by the X-ray CT apparatus 1 is used in the main scan performed by the X-ray CT apparatus 1. However, the position information generated by the X-ray CT apparatus 1 may be used in a main scan performed by another medical image diagnosis apparatus. Conversely, the X-ray CT apparatus 1 may use position information generated in a medical examination performed in the past by another medical image diagnosis apparatus. Accordingly, as a fourth embodiment, an example will be explained in which position information is managed with respect to mutually-different modalities. For example, the X-ray CT apparatus 1 according to the fourth embodiment is configured to set a scan range of the main scan by using position information appended to an image generated by an MRI apparatus. It is assumed that the MRI apparatus according to the fourth embodiment is provided with the same functions as those of the processing circuitry 37 illustrated in FIG. 2. In other words, the MRI apparatus according to the fourth embodiment is capable of executing the detecting function 37a, the position matching function 37b, the appending function 37c, and the controlling function 37d. For example, the MRI apparatus according to the fourth embodiment is configured to detect landmarks of the patient P from an image generated by using data acquired by performing a scan on the patient P. After that, on the basis of information related to the positions of landmarks, the MRI apparatus is configured to determine position information obtained by expressing the scan range for the patient P as an absolute position in the image taking system and further appends the determined position information to the image. For example, as the position information, the MRI apparatus determines "the reference position: the landmark C11 (the vertex); the landmark C1: 400 mm; the landmark C2: 600 mm; and the couchtop reference position: the landmark C11 (the vertex): 0 mm". In that situation, it is assumed that a mark has been put on the couchtop of the MRI apparatus, so that the patient P is placed on the couchtop in such a manner that the vertex is aligned with the mark.

A configuration of the X-ray CT apparatus 1 according to the fourth embodiment is the same as the configuration of the X-ray CT apparatus 1 according to the first embodiment, except that a part of the functions of the controlling function 37d is different. Thus, explanations about the constituent elements other than the controlling function 37d will be omitted. When there was at least one past medical examination performed on the patient P that includes the scan range of the scheduled scan, the controlling function 37d sets a scan range of the main scan by referring to the position information appended to a past image generated in the past medical examination. In this situation, the past image is an image generated by another medical image diagnosis apparatus such as the MRI apparatus. FIG. 20 is a drawing for explaining the fourth embodiment.

FIG. 20 illustrates a GUI screen in a situation where the chest is set as a target site during a protocol pre-set operation of the main scan. Further, FIG. 20 illustrates an example in which there was at least one past medical examination performed on the chest of the patient P by an MRI apparatus. In that situation, the controlling function 37d obtains an MR image of the medical examination performed by the MRI apparatus. Further, as illustrated in FIG. 20, the GUI screen displays, on the left side thereof, buttons (e.g., buttons representing the head, the chest, the abdomen, the lungs, the heart, and/or the like) used for designating a target site, as well as a virtual patient image rendering an entire human body, and the MR image. Further, FIG. 20 illustrates the situation where a scan range R20 corresponding to the chest has been set in the virtual patient image. In this situation, the controlling function 37d reads the position information appended to the obtained MR image and sets the scan range R20. In this situation, it is assumed that, when the scan range setting process is performed, the patient P is placed on the couchtop 22, in such a manner that the vertex of the patient P is aligned with the mark put on the couchtop 22. In this situation, for example, as the scan range to be used during the main scan, the controlling function 37d sets the range from the landmark C1 at an absolute position 400 mm of the image taking apparatus to the landmark C2 at the absolute position 600 mm of the image taking apparatus, as the scan range, while using the landmark C11 (the vertex) as the reference position. As a result of the scan range R20 being set in the virtual patient image, the position matching function 37b transforms the scan range R20 into coordinate information expressed in the MR image so as to set a scan range R21. It is possible to change, as appropriate, the scan range R20 set in the virtual patient image, by receiving an operation to enlarge or reduce the scan range R20 performed on the GUI by the operator.

Further, the controlling function 37d may be configured to cause the display 32 to display the past image and an image generated by the main scan so as to be superimposed on each other, on the basis of the position information appended to the past image. For example, on the basis of the position information appended to the MR image, the controlling function 37d causes the display 32 to display the MR image and a CT image generated by the main scan, so as to be superimposed on each other after the positions thereof are aligned with each other.

As explained above, in the fourth embodiment, the X-ray CT apparatus 1 is configured to set the scan range of the main scan scheduled to be performed on the patient P, by referring to the position information appended to the image generated by the other medical image diagnosis apparatus such as the MRI apparatus. With this arrangement, according to the fourth embodiment, it is possible to omit the position determining scan. As a result, it is possible to reduce the radiation exposure amount of the patient P. Further, the X-ray CT apparatus 1 according to the fourth embodiment may be configured to set the scan range of the main scan scheduled to be performed on the patient P, by referring to position information appended to an image generated by another X-ray CT apparatus. Further, the X-ray CT apparatus according to the fourth embodiment may have any of the scan range setting processes explained in the second and the third embodiments applied thereto.

Other Embodiments

The first to the fourth embodiments have thus been explained. The present disclosure may be carried out in various modes other than those described in the first to the fourth embodiments above.

Applications to Images Other than DICOM Images

Further, in the embodiments above, the example is explained in which the appending function 37c stores the determined position information into the DICOM tag attached to the DICOM image; however, possible embodiments are not limited to this example. For instance, the appending function 37c may append the determined position information to an image compliant with a standard used in the medical facility.

A Two-Dimensional (2D) Scanogram

In the embodiments above, the example is explained in which, during the scanogram image taking process, the scan controlling circuitry 33 takes the three-dimensional scanogram image by acquiring the projection data corresponding to the entire surrounding of the patient P, so that the detecting function 37a performs the AL analysis on the three-dimensional scanogram image; however, possible embodiments are not limited to this example. For instance, the scan controlling circuitry 33 may take a two-dimensional scanogram image during the scanogram image taking process, so that the detecting function 37a performs the AL analysis on the two-dimensional scanogram image. Further, the appending function 37c may determine position information obtained by expressing the scan range for the patient P as an absolute position in the image taking system, on the basis of a result of the AL analysis performed on the two-dimensional scanogram image.

A Fat-Suppressed Scan

Further, there are some situations in which an MRI apparatus performs a fat-suppressed scan. In that situation, the MRI apparatus may determine position information indicating a scan range of the fat-suppressed scan, on the basis of information related to positions of landmarks.

A Contrast-Enhanced Scan

Further, when a contrast-enhanced image taking process is performed, the appending function 37c may further append information indicating temporal phases to an image, on the basis of a time at which the image taking process is started. For example, the appending function 37c appends information indicating that the temporal phase is an arterial phase to images corresponding to the time period from the start of the contrast-enhanced image taking process to 40 seconds later, appends information indicating that the temporal phase is a venous phase to images corresponding to the time period from 40 seconds later to 80 seconds later, and appends information indicating a tumor to images corresponding to the time period after three minutes later.

Types of Data to be Appended

Further, the appending function 37c may perform an AL analysis on four-dimensional image data and append a result of the AL analysis to the four-dimensional image data. For example, the appending function 37c may append information indicating a state of the patient P such as an exhalation period or an inhalation period to the four-dimensional image data. In addition, the appending function 37c may also attach a result of the AL analysis to raw data. For example, the appending function 37c may append information indicating what landmark is rendered in which views (e.g., from the m-th view to the n-th view) of the raw data. Further, the appending function 37c may append information indicating a state of the patient P such as a supine position or a prone position, to a generated image.

In the embodiments described above, the example is explained in which the detecting function 37a is configured to perform the AL analysis by using the volume data of the position determining image or the volume data of the diagnosis-purpose image; however, possible embodiments are not limited to this example. For instance, the detecting function 37a may perform an AL analysis by using two-dimensional position determining image.

Further, in the embodiments above, the example is explained in which the scan range is set in the virtual patient image; however, possible embodiments are not limited to this example. For instance, the virtual patient image is not requisite, and the setting of the scan range may be received in a position determining image or a past image.

Further, in the embodiments described above, the example is explained in which the appending function 37c appends the determined position information to the image; however, possible embodiments are not limited to this example. For instance, the appending function 37c may store a medical examination ID, the image, and the determined position information that are kept in correspondence with one another, into the storage circuitry 35. In that situation, for example, the controlling function 37d searches in the medical examination history stored in the server apparatus 2, for example, for such a piece of medical examination information that has the same patient ID and the same scan range. In this situation, when having determined that there is at least one piece of medical examination found in the search, the controlling function 37d identifies the medical examination ID, obtains a past image generated in the medical examination, and obtains position information linked to the medical examination ID.

Further, in the embodiments described above, the X-ray CT apparatus is explained as an example of the medical image diagnosis apparatus; however, possible embodiments are not limited to this example. For instance, the medical image diagnosis apparatus may be an X-ray diagnosis apparatus, an ultrasound diagnosis apparatus, a Magnetic Resonance Imaging (MRI) apparatus, or the like.

The term "processor" used in the explanation above denotes, for example, a circuit such as a Central Processing Unit (CPU), a Graphics Processing Unit (GPU), an Application Specific Integrated Circuit (ASIC), or a programmable logic device (e.g., a Simple Programmable Logic Device [SPLD], a Complex Programmable Logic Device [CPLD], or a Field Programmable Gate Array [FPGA]). Each of the processors realizes the function thereof by reading a program stored in the storage circuitry 35 and executing the read program. Alternatively, it is also acceptable to directly incorporate the program into the circuit of each of the processors, instead of having the programs stored in the storage circuitry 35. In that situation, each of the processors realizes the function thereof by reading the program incorporated in the circuit thereof and executing the read program. The processors according to the present embodiments each do not necessarily have to individually be configured as a single circuit. It is also acceptable to structure a single processor by combining together a plurality of independent circuits so as to realize the functions thereof. Further, it is also acceptable to integrate the plurality of constituent elements illustrated in FIG. 2 into a single processor so as to realize the functions thereof.

The constituent elements of the apparatuses and the devices illustrated in the drawings in the embodiments above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

Further, it is possible to realize the controlling method explained in the embodiments described above, by causing a computer such as a personal computer or a workstation to execute a control computer program (hereinafter, "control program") prepared in advance. It is possible to distribute the control program via a network such as the Internet. Further, the control program may be executed as being recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like and being read from the recording medium by a computer.

As explained above, according to at least one aspect of the embodiments described above, it is possible to manage the accurate position information during the scans.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising:
setting circuitry configured to obtain position information of a plurality of landmarks that are referenced to a reference position corresponding to a predetermined region of a patient, the position information being obtained based on a first image generated by performing a first scan on the patient and indicating a distance between the reference position and at least one landmark of the plurality of landmarks along a body-axis direction of the patient, and the setting circuitry being configured to set a scan range to be used during a second scan performed in a different examination from an examination including the first scan by using the reference position in an image taking system used during the second scan and the distance; and
image generating circuitry configured to generate a second image by performing the second scan on the scan range.

2. The medical image diagnosis apparatus according to claim 1, wherein
the setting circuitry, in accordance with a scanned site, identifies the reference position in the image taking system used during the second scan based on the plurality of landmarks in the first image, and sets the scan range to be used during the second scan on a basis of the identified reference position in the image taking system used during the second scan and the position information.

3. The medical image diagnosis apparatus according to claim 1, wherein
the setting circuitry obtains the reference position in the image taking system used during the second scan, and sets the scan range to be used during the second scan on a basis of the reference position in a image taking system used during the first scan that is included in the position information and the reference position in the image taking system used during the second scan.

4. The medical image diagnosis apparatus according to claim 1, wherein, when a plurality of sites is to be scanned, the setting circuitry sets a plurality of scan ranges each of which is obtained by expressing a scan range of a corresponding one of the plurality of sites to be scanned as an absolute position in the image taking system used during the second scan.

5. The medical image diagnosis apparatus according to claim 1, wherein the image generating circuitry further reconstructs the second image under a reconstruction condition that is a same condition as a reconstruction condition used for the first image, the reconstruction of the second image being performed by using data acquired under a scan condition that is a same scan condition as a scan condition used for the first image.

6. The medical image diagnosis apparatus according to claim 1, wherein the image generating circuitry causes a predetermined display to display the first image and the second image so as to be superimposed on each other, the first image and the second image being superimposed on each other on a basis of the position information of the first image.

7. The medical image diagnosis apparatus according to claim 1, further comprising:
detecting circuitry configured to detect the plurality of landmarks of the patient from the first image generated by performing the first scan on the patient; and
generating circuitry configured to determine, with respect to the plurality of landmarks, the position information in the image taking system used during the first scan.

8. The medical image diagnosis apparatus according to claim 7, wherein
the generating circuitry stores, into storage circuitry, the position information so as to be kept in correspondence with the first image, and
the setting circuitry obtains the position information corresponding to the first image from the storage circuitry and sets the scan range to be used during the second scan.

9. The medical image diagnosis apparatus according to claim 7, wherein
the detecting circuitry detects the plurality of landmarks of the patient from the first image, when the second scan is started,
the generating circuitry determines, with respect to the plurality of landmarks, the position information in the image taking system used during the first scan, and
the setting circuitry obtains the position information determined by the generating circuitry and sets the scan range to be used during the second scan.

10. The medical image diagnosis apparatus according to claim 7, wherein the generating circuitry stores, into storage circuitry, the second image so as to be kept in correspondence with another position information indicating the scan range to be used during the second scan.

11. The medical image diagnosis apparatus according to claim 7, further comprising:
position matching circuitry configured to bring a position of one of the plurality of landmarks-in the first image into association with a position in a virtual patient based on an anatomical model of a human body, wherein
the generating circuitry further brings the position in the virtual patient into correspondence with the first image.

12. The medical image diagnosis apparatus according to claim 1, wherein the first image is an image generated by another medical image diagnosis apparatus.

13. The medical image diagnosis apparatus according to claim 1, wherein the reference position corresponds to a vertex of the patient.

14. The medical image diagnosis apparatus according to claim 1, wherein the setting circuitry is configured to obtain the position information of the plurality of landmarks that are referenced to the reference position corresponding to the predetermined region of the patient such that the position information indicates respective distances between the reference position and the plurality of landmarks along the body-axis direction of the patient.

15. The medical image diagnosis apparatus according to claim 14, wherein the reference position corresponds to a vertex of the patient.

* * * * *